(12) United States Patent
Jung et al.

(10) Patent No.: US 6,291,131 B1
(45) Date of Patent: Sep. 18, 2001

(54) MONOMERS FOR PHOTORESIST, POLYMERS THEREOF, AND PHOTORESIST COMPOSITIONS USING THE SAME

(75) Inventors: Jae Chang Jung; Chi Hyeong Roh; Min Ho Jung; Keun Kyu Kong; Geun Su Lee; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/383,547

(22) Filed: Aug. 26, 1999

(30) Foreign Application Priority Data

Aug. 26, 1998 (KR) .................................................. 98-34695

(51) Int. Cl.$^7$ ...................................................... G03F 7/004
(52) U.S. Cl. ...................... 430/270.1; 430/325; 430/315; 430/926; 526/271; 526/262
(58) Field of Search .............. 430/270.1, 281.1, 430/286.1, 905, 926; 526/328.1, 329.7, 317.1, 271

(56) References Cited

U.S. PATENT DOCUMENTS

| | | | |
|---|---|---|---|
| 3,370,047 | 2/1968 | Raines | 260/78.5 |
| 3,715,330 | 2/1973 | Nogami et al. | 260/40 R |
| 4,011,386 | 3/1977 | Matsumoto et al. | 526/259 |

(List continued on next page.)

FOREIGN PATENT DOCUMENTS

| | | | |
|---|---|---|---|
| 0071571 | 7/1982 | (EP) . | |
| 0291970 | 11/1988 | (EP) | C08F/210/02 |
| 0789278A2 | 2/1997 | (EP) . | |
| 794458 A2 | 9/1997 | (EP) . | |
| 0836119A1 | 11/1997 | (EP) . | |
| 878738 * | 11/1998 | (EP) . | |
| 0878738A2 | 11/1998 | (EP) | G03F/7/004 |
| 0768813 | 2/1957 | (GB) . | |
| 1329997 | 9/1970 | (GB) . | |

(List continued on next page.)

OTHER PUBLICATIONS

D. Braun and Joannis Pomakis, Uber Die Copolymerisation von Maleinsaureanhydrid Mit Bicyclo [2.2.1] Hept–5–En–2–Carbonsaure, *European Polymer Journal,* (1974) vol. 10 [4] pp. 357–365. (Abstract only in English).

J. Byers et al., Recent Advancements in Cycloolefin Based Resists for ArF Lithography, *Journal of Photopolymer Science and Technology,* (1998) vol. II No. 3, pp. 465–474.

James V. Crivello and Sang–Yeon Shim, Chemically Amplified Electron–Beam Photoresists, *Chemical Mater.,* (1966) vol. 8, pp. 376–381.

(List continued on next page.)

*Primary Examiner*—Janet Baxter
*Assistant Examiner*—Yvette M. Clarke
(74) *Attorney, Agent, or Firm*—Townsend and Townsend and Crew LLP

(57) ABSTRACT

The present invention relates to novel monomers for preparing photoresist polymers, polymers thereof, and photoresist compositions using the same. The monomers of the iinvention are represented by the following Chemical Formula 1:

Chemical Formula 1

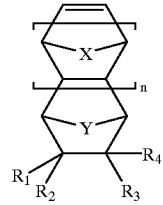

wherein, X and Y individually represent oxygen, sulfur, $CH_2$ or $CH_2CH_2$; n is an integer of 1 to 5; and $R_1$, $R_2$, $R_3$ and $R_4$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain, $C_1$–$C_{10}$ alkyl having substituent(s) including one or more hydroxyl group(s) on its main or branched chain, $C_1$–$C_{10}$ ester having substituent(s) including one or more hydroxyl group(s ) on its main or branched chain, $C_1$–$C_{10}$ ketone having substituent(s) including one or more hydroxyl group(s) on its main or branched chain, $C_1$–$C_{10}$ carboxylic acid having substituent(s) including one or more hydroxyl group(s) on its main or branched chain, or $C_1$–$C_{10}$ acetal having substituent(s) including one or more hydroxyl group(s) on its main or branched chain; provided that at least one of $R_1$ to $R_4$ represent(s) —COO—R'—OH wherein R' is a linear or branched chain alkyl group with or without substituent(s) on its linear or branched chain. Polymers according to the present invention preferably comprise (i) a monomer of Chemical Formula 1 above as the first comonomer, (ii) a polyalicyclic derivative having one or more acid labile protective group(s) as the second comonomer, and (iii) at least one polymerization-enhancing monomer, preferably selected from the group consisting of maleic anhydride, maleimide derivatives, and combinations thereof. In order to increase photosensitivity, it is also preferable for the photoresist copolymer to comprise (iv) a polyalicyclic derivative having one or more carboxylic acid groups, as an additional comonomer.

32 Claims, No Drawings

U.S. PATENT DOCUMENTS

| | | | |
|---|---|---|---|
| 4,106,943 | 8/1978 | Ikeda et al. | 96/115 R |
| 4,126,738 | 11/1978 | Gaylord | 526/271 |
| 4,202,955 | 5/1980 | Gaylord | 526/272 |
| 4,440,850 | 4/1984 | Paul et al. | 430/325 |
| 4,491,628 | 1/1985 | Ito et al. | 430/176 |
| 4,857,435 | 8/1989 | Hopf et al. | 430/192 |
| 4,883,740 | 11/1989 | Schwalm et al. | 430/270 |
| 4,948,856 | 8/1990 | Minchak et al. | 526/281 |
| 4,986,648 | 1/1991 | Kobayashi et al. | 351/160 R |
| 5,064,919 | 11/1991 | Hara et al. | 526/169 |
| 5,087,677 | 2/1992 | Brekner et al. | 526/160 |
| 5,212,043 | 5/1993 | Yamamoto et al. | 430/192 |
| 5,252,427 | 10/1993 | Bauer et al. | 430/270 |
| 5,278,214 | 1/1994 | Moriya et al. | 524/238 |
| 5,585,219 | 12/1996 | Kaimoto et al. | 430/270.1 |
| 5,738,975 | 4/1998 | Nakano et al. | 430/280.1 |
| 5,843,624 | 12/1998 | Houlihan et al. | 430/296 |
| 5,849,808 | 12/1998 | Schacht et al. | 522/31 |
| 6,028,153 | 2/2000 | Jung | 526/258 |
| 6,045,967 | 4/2000 | Jung et al. | 430/270.1 |
| 6,048,664 | 4/2000 | Houlihan et al. | 430/270.1 |
| 6,071,670 | 6/2000 | Ushirogouchi et al. | 430/270.1 |
| 6,103,449 | * 8/2000 | Sato | 430/270.1 |
| 6,121,340 | * 9/2000 | Shick et al. | 522/31 |
| 6,132,926 | 10/2000 | Jung et al. | |
| 6,136,499 | * 10/2000 | Goodall et al. | 430/270.1 |
| 6,147,177 | * 11/2000 | Jayaraman et al. | 526/281 |
| 6,150,069 | 5/1999 | Jung et al. | |
| 6,159,655 | * 12/2000 | Sato | 430/270.1 |
| 6,165,672 | 9/1998 | Jung et al. | |
| 6,225,020 | 4/1999 | Jung et al. | |

FOREIGN PATENT DOCUMENTS

| | | | |
|---|---|---|---|
| 1342112 | 12/1973 | (GB) | |
| 1484061 | 8/1997 | (GB) | C08J/3/28 |
| 1335095 | 10/1997 | (GB) | C05G/20/00 |
| 2320501A | 6/1998 | (GB) | |
| 2320717A | 7/1998 | (GB) | |
| 2320718A | 7/1998 | (GB) | |
| 2321060A | 7/1998 | (GB) | |
| 2332679A | 6/1999 | (GB) | C08F/232/08 |
| 2336845A | 11/1999 | (GB) | C08F/222/06 |
| 2336846A | 11/1999 | (GB) | C08F/222/40 |
| 04099967 | 4/1992 | (JP) | |
| 10316720 | 2/1998 | (JP) | |
| WO 96/37526 | 11/1996 | (WO) | |
| WO 97/33198 | 9/1997 | (WO) | |
| WO 98/07759 | 2/1998 | (WO) | C08F/2/50 |
| WO 99/14256 | 3/1999 | (WO) | |

OTHER PUBLICATIONS

F. M. Houlihan et al., Photo Generators of Sulfamic Acids; Use in Chemically Amplified Single Layer Resists, *Journal of Photopolymer Science and Technology* (1998) vol. 11, No. 3, pp. 419–430.

Uzodinma Okoroanyanwu et al., New Single Layer Positive Photoresists for 193 nm Photolithography, *SPIE*, vol. 3049, 1997, pp. 92–103.

35–Synthetic High Polymers, *Chemical Abstracts*, (1967) vol. 66, 76325, pp. 7178–7179.

CA Abstract 130: 229879 only: (Min–Ho Jung et al., Synthesis and Characterization of Alicyclic Polymers With Hydrophilic Groups for 193 nm Single Layer Resist, *Japanese Journal of Applied Physics* (1999).

CA Register No. 37503–43–8 No date.

WPI Accession No. 94–227160[28] (FR2695540) No date.

WPI Accession No. 99–076491 (JP10316720) No date.

Japanese Patent Abstract 10017526 No date.

Japanese Patent Abstract 08134015 A No date.

CA 121:10910 (JP 05310885) No date.

CA 129:209337 (JP 10–218941) No date.

CA 129: 223219 (JP 10213912) No date.

CA 130:229879 No date.

CA 1981 47831 No date.

ACS Abstract Ref. 172992–05–1 No date.

Thomas I. Wallow, et al., "Evaluation of Cycloolefin–Maleic Anhydride Alternating Copolymers as Single–Layer Photoresist for 193nm Photolithography", 1996, Proc. SPIE, vol. 2724, 355–364.

R.D. Allen et al., "The Influence of Photoacid Structure on the Design and Performance of 193nm Resists", 1997, Journal of Photopolymer Science and Technology, vol. 10, 503–510.

F.M. Houlihan et al., "A Commercially Viable 193nm single Layer Resist Platform", 1997, Journal of Photopolymer Science and Technology, vol. 10, 511–520.

J.C. Jung et al., "ArF Single Layer Resist Composed of Alicyclic Main Chain Containing Maleic Anhydride", 1997, Journal of Photopolymer Science and Technology, vol. 10, 529–533.

S.J. Choi et al., "New ArF Single–layer Resist for 193–nm Lithography", 1997, Journal of Photopolymer Science and Technology, vol. 10, 521–528.

T. Hattori et al., "Synthesis and Dissolution Characteristics of Novel Alicyclic Polymer With Monoacid Ester Structures". 1997, Journal of Photopolymer Science and Technology, vol. 10, 535–544.

K. Nozaki and Ei Yaro, "New Protective Groups in Methacrylate Polymer for 193–nm Resists", 1997, Journal of Photopolymer Science and Technology, vol. 10, 545–550.

K. Nakano et al., "Chemically Amplified Resist Based on High Etch–Resistant Polymer for 193–nm Lithography", 1997, Journal of Photopolymer Science and Technology, vol. 10, 561–569.

Alexander A. Dobrev, Emile Perez, Jean Claud Ader, Armand Lattes, "First Application of Functionalized in the Ester Moiety Acrylates in Diels–Alder Reaction: Invluence of Solvents on Stereochemistry"; Bulgarian Chemical Communications, vol. 28, No. 2 (1995) pp. 253–258.

T.P. McGovern and C.E. Schreck, "Mosquito Repellents: Monocarboxylic Esters of Aliphatic Diols", Journal of the American Mosquito Control Association, vol. 4, No. 3, pp. 314–321.

CA Register No. 100207–98–5. No date.

CA Register No. 32759–57–2. No date.

CA Register No. 27056–70–8. No date.

CA Register No. 174659–58–6. No date.

CA Register No. 28503–41–5. No date.

CA Register No. 194997–59–6. No date.

CA Abstract No. 104:149512 & Macromolecules 19(4) 1266–8 (1986).

CA Abstract No. 91:124064 & Makromol. Chem. 180(8) 1975–88 (1979).

CA Abstract No. 113:24734 & JP 02 051511. No date.
CA Abstract No. 127:227269 & J Photopolym. Sci. Technol. 10(4) 529–534 (1997).
CA Abstract No. 124:317926 & Macromol. Rapid Commun. 17(3) 173–180 (1996).
CA Abstract No. 124:203171 & Macromolecules 29(8) 2755–63 (1996).

CA Abstract No. 127:227308 & Proc. SPIE–Int. Soc. Opt. Eng. (1997) 3049 Advances in Resist Technology and Processing XIV 92–103.
CA Abstract No. 66:18889 & Magy. Kem. Foly. (1966) 72(11)491–3.

* cited by examiner

MONOMERS FOR PHOTORESIST, POLYMERS THEREOF, AND PHOTORESIST COMPOSITIONS USING THE SAME

FIELD OF THE INVENTION

The present invention relates to novel monomers for preparing photoresist polymers, photoresist polymers and photoresist compositions using the same. More specifically, it relates to such monomers, polymers and compositions which are usable in a photolithography process employing a KrF (248 nm), ArF (193 nm), E-beam, ion-beam or EUV light source, in the preparation of a microcircuit of a highly integrated semiconductor element.

BACKGROUND OF THE INVENTION

Recently, chemical amplification type DUV (deep ultra violet) photoresists have been investigated as a means for achieving high sensitivity in micro processes for preparing a semiconductor device. These photoresists are generally prepared by blending a photoacid generator with photoresist polymer matrix macromolecules having acid labile substituents in an organic solvent to form a photoresist composition.

According to the reaction mechanism of such photoresists, the photoacid generator generates acid when it is irradiated by the light source, and substituents on the main chain or branched chain of the matrix macromolecule in the exposed portion react with the generated acid to be decomposed or cross-linked, thereby considerably altering the polarity of the macromolecule. As a result, there is a solubility difference in the developing solution between the exposed area and the unexposed area. For example, in case of a positive photoresist, the main or branched chain of the matrix macromolecule is decomposed by acid in the exposed area and is removed by being dissolved in the developing solution. On the other hand, in the case of the unexposed area, the original structure of the macromolecular compound is maintained without being dissolved in the developing solution. As a result, the image of a mask is formed on the substrate as a positive image. In the lithography process, resolution depends upon the wavelength of the light source—the shorter the wavelength, the more minute the pattern that can be formed.

A suitable photoresist polymer generally requires excellent etching resistance, heat resistance and adhesiveness, and, in particular, when a photoresist is used for lithography processes employing ArF light source, it should be developable in 2.38% aqueous tetramethylammonium hydroxide (TMAH) solution. However, it is very difficult to synthesize a polymer that satisfies all these requisites. For example, a polymer having a polyacrylate main chain can be easily synthesized, but it has poor etching resistance and difficulties in the developing process. Etching resistance can be enhanced if an alicyclic monomer is introduced into the main chain. However, it is very difficult to synthesize a polymer having a main chain comprised of all alicyclic monomers.

Research to solve the problems described above has been widely performed in the past. In the case of forming an ultramicro pattern of 0.10 micron or less, the thickness of the photoresist layer must be 0.3 micron or less, but no photoresist has been developed to date which is resistant to etching gas in such a thin layer. In other words, any photoresist composition developed up to the present shows insufficient adhesiveness to the substrate and etching resistance when it is applied as a photoresist layer for a semiconductor element requiring resolution of 0.1 μm or less.

SUMMARY OF THE INVENTION

An object of the present invention is to provide novel monomers which are suitable for forming polymers which can be used as photoresists in the formation of high integrity integrated circuits, and processes for preparing the same.

Another object of the present invention is to provide novel photoresist polymers comprising said monomers, and a process for preparing the same.

Still another object of the present invention is to provide photoresist compositions containing the novel polymers, and a process for preparing the same.

In order to achieve these objects, the present invention provides a novel monomer represented by the following Chemical Formula 1:

Chemical Formula 1

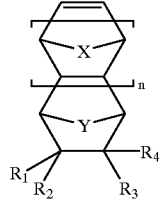

wherein, X and Y individually represent oxygen, sulfur, $CH_2$ or $CH_2CH_2$; n represents an integer of 1 to 5; and $R_1$, $R_2$, $R_3$ and $R_4$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain, $C_1$–$C_{10}$ alkyl having substituent(s) including one or more hydroxyl group(s) on its main or branched chain, $C_1$–$C_{10}$ ester having substituent(s) including one or more hydroxyl group(s) on its main or branched chain, $C_1$–$C_{10}$ ketone having substituent(s) including one or more hydroxyl group(s) on its main or branched chain, $C_1$–$C_{10}$ carboxylic acid having substituent(s) including one or more hydroxyl group(s) on its main or branched chain, or $C_1$–$C_{10}$ acetal having substituent(s) including one or more hydroxyl group(s) on its main or branched chain; provided that at least one of $R_1$ to $R_4$ represent(s) —COO—R'—OH wherein R' is a linear or branched chain alkyl group with or without substituent(s) on its linear or branched chain.

Further, in order to achieve another object of the present invention, a novel photoresist polymer is provided which comprises repeating units derived from the monomer of Chemical Formula 1. Preferred polymers of the present invention contain repeating units of Chemical Formula 1 in addition to one or more other repeating units, as represented by the following Chemical Formula 300:

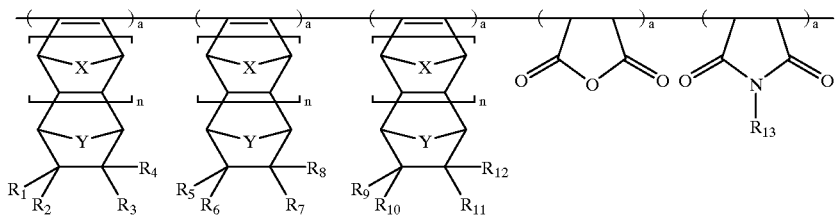

Chemical Formula 300 wherein, X, Y, V, W, U and Z individually represent oxygen, sulfur, $CH_2$ or $CH_2CH_2$; n represents an integer from 1 to 5, m and 1 individually represent an integer of 0 to 5; $R_1$ to $R_{12}$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain, $C_1$–$C_{10}$ alkyl having substituent(s) including one or more hydroxyl group(s) on its main or branched chain, $C_1$–$C_{10}$ ester having substituent(s) including one or more hydroxyl group(s) on its main or branched chain, $C_1$–$C_{10}$ ketone having substituent(s) including one or more hydroxyl group(s) on its main or branched chain, $C_1$–$C_{10}$ carboxylic acid having substituent(s) including one or more hydroxyl group(s) on its main or branched chain, or $C_1$–$C_{10}$ acetal having substituent(s) including one or more hydroxyl group(s) on its main or branched chain; a, b, c, d and e individually represent polymerization ratio of each comonomer that is present; and $R_{13}$ is a linear or branched alkyl group; provided that at least one of $R_1$ to $R_4$ represent(s) —COO—R'—OH wherein R' is an alkyl group having substituent(s) on its linear or branched chain, at least one of $R_5$ to $R_8$ represent(s) —R"—COO—R wherein R" is a linear or branched alkyl group and R is an acid labile protective group, and at least one of $R_9$ to $R_{12}$ represent(s) —R'"—COOH wherein R'" is a linear or branched alkyl group.

In order to achieve still another object, the present invention provides a photoresist composition that comprises said photoresist copolymer, a photoacid generator and an organic solvent.

DETAILED DESCRIPTION OF THE INVENTION

Novel Photoresist Monomers

The present inventors have found the polyalicyclic monomers of the invention, especially, polyalicyclic monomers which contain oxygen or sulfur in the ring and one or more hydroxyl group(s) as substituent(s), as represented by Chemical Formula 1, provide photoresist copolymers having excellent etching resistance as well as excellent adhesiveness to a substrate.

As previously stated, the monomers of the present invention are represented by the following Chemical Formula 1:

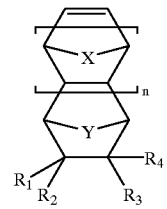

Chemical Formula 1 wherein X,Y, n, $R_1$, $R_2$, $R_3$, and $R_4$ are defined as set forth above. In preferred monomers of Chemical Formula 1, n is 1, and $R_1$, $R_2$, and $R_3$ is each hydrogen and $R_4$ is —COO—$CH_2CH_2$—OH or —COO—$CH_2CH_2CH_2$—OH.

Compounds of Chemical Formula 1 can be synthesized by means of various processes, but it is usually obtained by utilizing a Diels-Alder reaction. For example, when X and Y are different elements, the process comprises the two steps of (i) performing a Diels-Alder reaction with a compound of the following Chemical Formula 2:

Chemical Formula 2 and a compound of the following Chemical Formula 3:

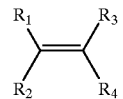

Chemical Formula 3 to give a compound of the following Chemical Formula 2x:

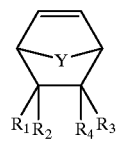

Chemical Formula 2x and; (ii) performing a Diels-Alder reaction with the resultant compound of Chemical Formula 2x and a compound of the following Chemical Formula 4:

Chemical Formula 4 to obtain a compound of Chemical Formula 1.

In the above Formulas 2, 3, 2x, and 4, X, Y, and $R_1$ to $R_4$ are identical to those defined in Chemical Formula 1 above.

When X and Y represent identical elements, the compound of Chemical Formula 1 can be obtained by performing the above-described Diels-Alder reaction with an excess amount of the compound of Chemical Formula 2 relative to the compound of Chemical Formula 3.

Photoresist Copolymers

As stated above, the polymers of the present invention are represented by the following Chemical Formula 300:

$R_8$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain, $C_1$–$C_{10}$ alkyl having substituent(s) including one or more hydroxyl group(s) on its main or branched chain, $C_1$–$C_{10}$ ester having substituent(s) including one or more hydroxyl group(s) on its main or branched chain, $C_1$–$C_{10}$ ketone having substituent(s) including one or more hydroxyl group(s) on its main or branched chain, $C_1$–$C_{10}$ carboxylic acid having substituent(s) including one or more hydroxyl group(s) on its main or branched chain, or $C_1$–$C_{10}$ acetal having substituent(s) including one or more hydroxyl group(s) on its main or branched chain; provided that at least one Chemical Formula 300

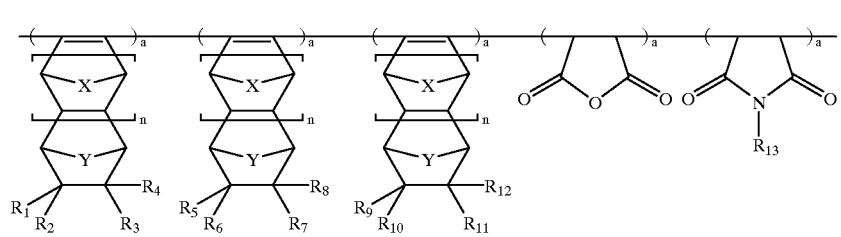

wherein, X, Y, V, W, U, Z, n, m, l, a, b, c, d, e, and $R_1$ to $R_{13}$ are as defined above. In one embodiment, the polymers of Chemical Formula 300 above comprise the repeating units represented by a and b and/or c, and optionally comprise the units represented by d and/or e. In another preferred embodiment, the polymers of Chemical Formula 300 comprise polyalicyclic repeating units wherein each of n, m and l is 1.

Since the compounds of Chemical Formula 1 are alicyclic compounds, their use as photoresist comonomers results in photoresist copolymers having a main chain comprised solely of repeating alicyclic units, thereby enhancing the etching resistance of the photoresist. In addition, the pendant hydroxyl group of the monomers of the present invention enhances adhesiveness between the photoresist and the substrate, so that an ultramicro pattern can be formed.

When a copolymer of the present invention is used as a chemical amplification-type photoresist, it is preferable to include as an additional comonomer with the monomer of Chemical Formula 1, an alicyclic derivative having an acid labile protective group, as represented by the following Chemical Formula 5 (hereinafter sometimes referred to as the second comonomer):

of $R_5$ to $R_8$ represent(s) —R"—COO—R wherein R" is a linear or branched alkyl group, and R is an acid labile protective group.

Acid labile groups are blocking or protective groups known to the art that are cleavable by the photoacid generator used in the photoresist composisiton. Any photoacid cleavable group is suitable in the practice of the invention so long as the polymerization reaction is not substantially inhibited thereby. Preferred acid labile groups are include tert-butyl (or 1,1-dimethylethyl), 2-tetrahydropyranyl, 2-tetrahydrofuranyl, ethoxyethyl and the like.

Additionally, in order to use a copolymer of the present invention as a chemical amplification-type photoresist in a photolithography process employing a light source of extremely short wavelength, i.e., 250 nm or less, exposure of the photoresist must be accomplished with small amounts of light energy. Thus, when such light sources are used, it is preferable to also incorporate in the photoresist copolymer an additional alicyclic monomer having one or more carboxylic acid groups, as represented by the following Chemical Formula 6 (hereinafter referred to as the third comonomer):

Chemical Formula 5

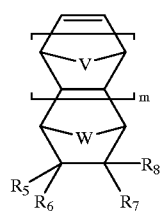

Chemical Formula 6

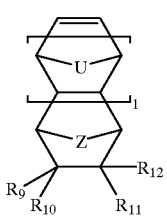

wherein V and W individually represent oxygen, sulfur, $CH_2$ or $CH_2CH_2$; m is an integer of 0 to 5; and $R_5$, to wherein U and Z individually represent oxygen, sulfur, $CH_2$ or $CH_2CH_2$; l is an integer of 0 to 5; and $R_9$ to $R_{12}$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain, $C_1$–$C_{10}$ alkyl having substituent(s) including one or more hydroxyl group(s) on its main or branched chain, $C_1$–$C_{10}$ ester having substituent(s) including one or more hydroxyl group(s) on its main or branched chain, $C_1$–$C_{10}$ ketone having substituent(s) including one or more hydroxyl group(s) on its main or branched chain, $C_1$–$C_{10}$ carboxylic acid having substituent(s) including one or more hydroxyl group(s) on its main or branched chain, or $C_1$–$C_{10}$ acetal having substituent(s) including one or more hydroxyl group(s) on its main or branched chain; provided that at least one of $R_9$ to $R_{12}$ represent(s) —R'"—COOH wherein R'" is a linear or branched alkyl group.

Polymerization with only the alicyclic compounds such as those represented by Chemical Formula 1, 5 or 6 can be performed using known polymerization methods, for example using a metal catalyst system as described in Goodall et al, International Publication Number WO 96/37526. However, the preferred polymerization method for the practice of the present invention is to incorporate one or more additional monomers (hereinafter referred to as the polymerization-enhancing comonomers) to increase the yield of copolymer. The most preferred polymerization-enhancing comonomers are maleic anhydride, having the following Chemical Formula 7:

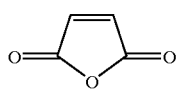

Chemical Formula 7 and/or a maleimide derivative of Chemical Formula 8:

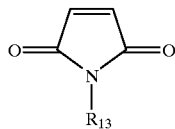

Chemical Formula 8 wherein $R_{13}$ is a linear or branched alkyl group.

Synthetic processes for preparing the second comonomers described above are set forth in Examples 17 to 41. Synthetic processes for preparing the third comonomers described above are set forth in Examples 42 to 75. The polymerization-enhancing monomers may be commercially obtained or prepared by known processes. It is understood that any suitable synthetic process may be used to prepare the above comonomers and the invention is not intended to be limited to the Examples set forth herein.

Synthesis of Photoresist Copolymer

Preferred photoresist copolymers according to the present invention are prepared by radical polymerization of the monomers described above using a conventional radical polymerization initiator.

As previously stated, copolymers according to the present invention preferably comprise (i) an alicyclic derivative having one or more acid labile protective group(s), as the first comonomer, (ii) an alicyclic derivative having one or more hydroxyl group(s), more preferably a hydroxy alkyl carboxylate group (—COO—R'—OH wherein R' is an alkyl group), as the second comonomer, and (iii) at least one polymerization-enhancing monomer, preferably selected from the group consisting of maleic anhydride and maleimide derivatives, and combinations thereof. In order to increase photosensitivity, it is also preferable for the photoresist copolymer to comprise (iv) an alicyclic derivative having one or more carboxylic acid groups, as an additional comonomer.

Photoresist copolymers according to the present invention are preferably obtained by conventional bulk polymerization or solution polymerization of the comonomers. As the organic solvent for the polymerization, cyclohexanone, methyl ethyl ketone, benzene, toluene, dioxane, tetrahydrofuran or dimethylformamide may be used as a single solvent or a mixed solvent. As the polymerization initiator, a conventional radical polymerization initiator such as benzoyl peroxide, 2,2'-azobisisobutyronitrile (AIBN), acetyl peroxide, lauryl peroxide, tert-butyl peracetate, or the like may be used.

Preferred photoresist copolymers according to the present invention, and processes for preparing them are disclosed in Examples 76 to 101; however, the present invention is not limited to those Examples.

Preparation of Photoresist Compositions and Formation of Photoresist Patterns

A photoresist composition can be prepared by mixing a novel photoresist polymer according to the present invention with a conventional organic solvent and conventional photoacid generator.

For example, a photoresist polymer according to the present invention may be dissolved in a solvent such as propylene glycol methyl ether acetate. The amount of the polymer is preferably 1 to 30% by weight of the solvent. A photoacid generator such as an onium salt or an organic sulfonic acid is then blended into the resultant solution in an amount of 0.1 to 10% by weight of the polymer and the solution is filtered through an ultramicro filter to provide the photoresist composition.

Other organic solvents, e.g. ethyl 3-ethoxypropionate, methyl 3-methoxypropionate or cyclohexanone, may be used instead of propylene glycol methyl ether acetate. Typical photoacid generators include triphenylsulfonium triflate or dibutylnaphthyl sulfonium triflate.

The photoresist composition prepared according to the present invention may be spin-coated on a silicon wafer to form a thin photoresist film. The coated wafer may then soft-baked in an oven or on a hot plate at 80 to 1500° C. for 1 to 5 minutes, and exposed to patterned light by using a deep ultraviolet exposer or an excimer laser exposer. ArF, KrF, E-beam, EUV, ion beam, or the like may be used as the light source.

After light-exposure, the wafer may be impregnated in a developing solution such as 2.38% aqueous TMAH solution for 1.5 minutes, and post-baked at 100° C. to 2000° C. to obtain an ultramicro photoresist image having excellent etching resistance, photosensitivity and adhesiveness.

DETAILED DESCRIPTION OF PREFERRED EMBODIMENTS

The invention is described in more detail by referring to the examples below, but it should be noted that the present invention is not in any way intended to be limited to such examples.

EXAMPLE 1

Tetrahydrofuran solvent (500 g), thiophene (1.0 mole), represented by Chemical Formula 2a below, ethylene glycol (0.22 mole) and 2-hydroxyethyl acrylate (1.2 mole), represented by Chemical Formula 3a, are introduced into a 2-liter flask, and the mixture is stirred at 70° C. for 24 hours. After the reaction is completed, the solvent and excess 2-hydroxyethyl acrylate are removed by using a rotary evaporator, and the residue is distilled in vacuo to obtain pure 2-hydroxyethyl 7-thiabicyclo[2.2.1]hept-5-ene-2-carboxylate represented by Chemical Formula 101 below (yield: 80%).

Chemical Formula 2a:

Chemical Formula 3a:

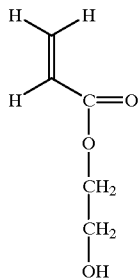

Chemical Formula 101:

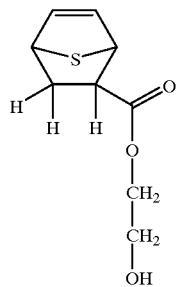

EXAMPLE 2

The procedure of Example 1 is repeated but using furan (1 mole) instead of thiophene (1.0 mole), to obtain pure 2-hydroxyethyl 7-oxabicyclo[2.2.1]hept-5-ene-2-carboxylate, represented by Chemical Formula 102 below (yield: 85%).

Chemical Formula 102

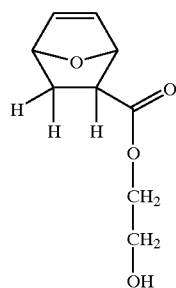

EXAMPLE 3

Tetrahydrofuran solvent (500 g), pure 2-hydroxyethyl 7-thiabicyclo[2.2.1]hept-5-ene-2-carboxylate (1 mole) of Chemical Formula 101 obtained from Example 1, and furan (1 to 6 mole) are introduced into an autoclave. The mixture is reacted at a temperature of 130 to 1500 C. and a pressure of 10 to 30 atm for 10 hours. After the reaction is completed, the reaction mixture is distilled in vacuo to obtain the compound represented by the following Chemical Formula 103:

Chemical Formula 103

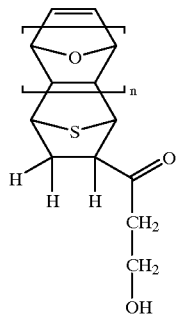

The value 'n' of Chemical Formula 103 changes depending on the amount of furan introduced; i.e. the 'n' value of the final product approximately increases by 1 with every 1.2 mole increase of furan.

EXAMPLE 4

The procedure of Example 3 is repeated but using 2-hydroxyethyl 7-oxabicyclo[2.2.1]hept-5-ene-2-carboxylate (1 mole) of Formula 102 obtained from Example 2, instead of 2-hydroxyethyl 7-thiabicyclo[2.2.1]hept-5-ene-2-carboxylate (1 mole), and thiophene (1 to 6 mole) instead of furan (1 to 6 mole), to obtain the compound of following Chemical Formula 104:

Chemical Formula 104

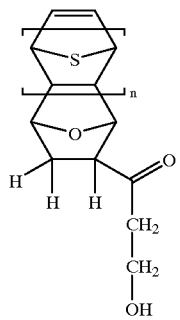

EXAMPLE 5

The procedure of Example 3 is repeated but using thiophene (1 to 6 mole) instead of furan (1 to 6 mole), to obtain the compound of the following Chemical Formula 105:

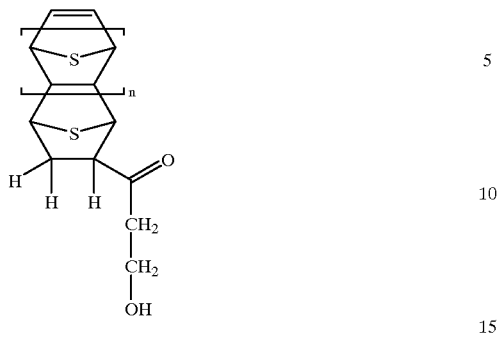

Chemical Formula 105

EXAMPLE 6

The procedure of Example 3 is repeated but using 2-hydroxyethyl 7-oxabicyclo[2.2.1]hept-5-ene-2-carboxylate (1 mole) instead of 2-hydroxyethyl 7-thiabicyclo[2.2.1]hept-5-ene-2-carboxylate (1 mole), to obtain the compound of the following Chemical Formula 106:

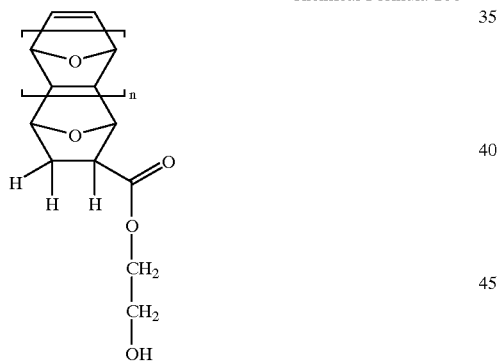

Chemical Formula 106

EXAMPLE 7

Tetrahydrofuran solvent (500 g), 2-hydroxyethyl bicyclo [2.2.1]hept-5-ene-2-carboxylate and furan (1 to 6 mole) are introduced to an autoclave. The mixture is reacted at a temperature of 130 to 150° C. and a pressure of 10 to 30 atm for 10 hours. After the reaction is completed, the reaction mixture is distilled in vacuo to obtain the compound represented by the following Chemical Formula 107:

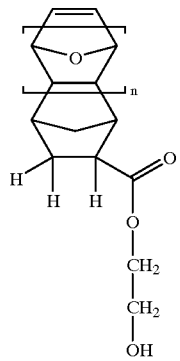

Chemical Formula 107

EXAMPLE 8

The procedure of Example 7 is repeated but using thiophene (1 to 6 mole) instead of furan (1 to 6 mole), to obtain the compound of the following Chemical Formula 108:

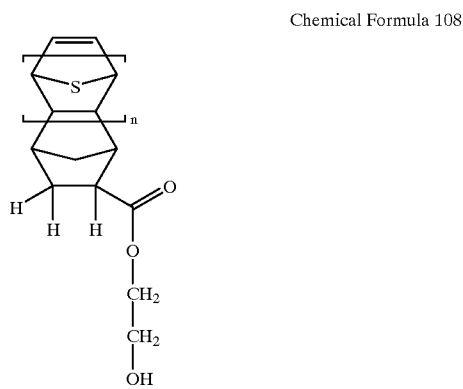

Chemical Formula 108

EXAMPLE 9

Tetrahydrofuran solvent (500 g), 3-hydroxypropyl acrylate (1.2 mole) of Chemical Formula 3b below, and thiophene (1.0 mole) are introduced to a 2-liter flask, and the mixture is stirred at 70° C. for 24 hours. After the reaction is completed, the solvent and excess amount of 3-hydroxypropyl acrylate were removed by using a rotary evaporator. The residue is distilled in vacuo to obtain pure 3-hydroxypropyl 7-thiabicyclo[2.2.1]hept-5-ene-2-carboxylate represented by Chemical Formula 109 (yield: 80%).

Chemical Formula 3b

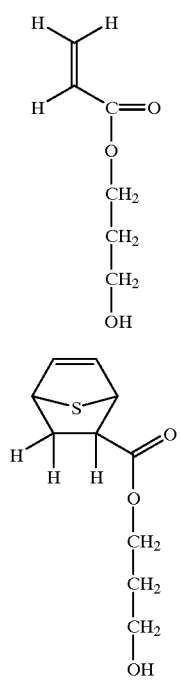

Chemical Formula 109

EXAMPLE 10

The procedure of Example 9 is repeated but using furan (1 mole) instead of thiophene (1.0 mole), to obtain pure 3-hydroxypropyl 7-oxabicyclo[2.2.1]hept-5-ene-2-carboxylate (yield: 85%) represented by the following Chemical Formula 110:

Chemical Formula 110

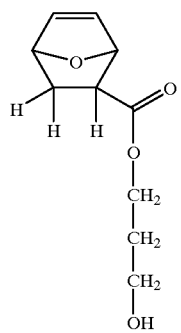

EXAMPLE 11

Tetrahydrofuran solvent (500 g), the compound of Chemical Formula 109 obtained from Example 9 (that is, 3-hydroxypropyl 7-thiabicyclo[2.2.1]hept-5-ene-2-carboxylate, 1 mole) and furan (1 to 6 mole) are introduced to an autoclave, and the mixture is reacted at a temperature of 130 to 150° C. and a pressure of 10 to 30 atm for 10 hours. After the reaction is completed, the reaction mixture is distilled in vacuo to obtain the compound represented by the following Chemical Formula 111:

Chemical Formula 111

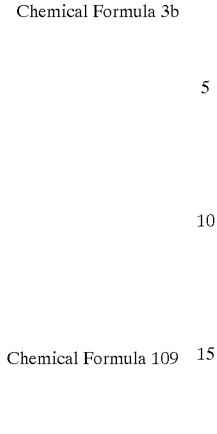

The value 'n' changes depending on the amount of furan introduced; i.e. the 'n' value of the final product approximately increases by 1 with every 1.2 mole increase of furan.

EXAMPLE 12

The procedure of Example 11 is repeated but using 3-hydroxypropyl 7-oxabicyclo[2.2.1]hept-5-ene-2-carboxylate (1 mole) instead of 3-hydroxypropyl 7-thiabicyclo[2.2.1]hept-5-ene-2-carboxylate (1 mole), and thiophene (1 to 6 mole) instead of furan (1 to 6 mole), to obtain the compound of the following Chemical Formula 112:

Chemical Formula 112

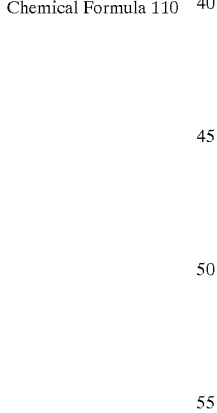

EXAMPLE 13

The procedure of Example 11 is repeated but using thiophene (1 to 6 mole) instead of furan (1 to 6 mole), to obtain the compound of the following Chemical Formula 113:

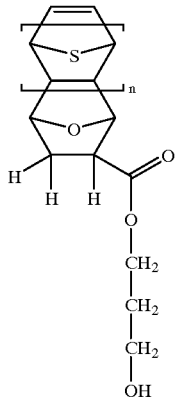

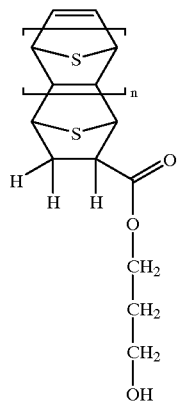

Chemical Formula 113

EXAMPLE 14

The procedure of Example 11 is repeated but using 3-hydroxypropyl 7-oxabicyclo[2.2.1]hept-5-ene-2-carboxylate (1 mole) instead of 3-hydroxypropyl 7-thiabicyclo[2.2.1]hept-5-ene-2-carboxylate (1 mole), to obtain the compound of the following Chemical Formula 114:

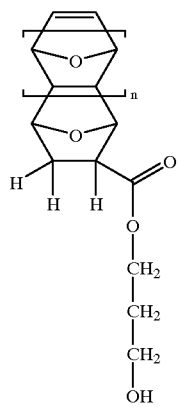

Chemical Formula 114

EXAMPLE 15

Tetrahydrofuran solvent (500 g), 3-hydroxypropylbicyclo[2.2.1]hept-5-ene-2-carboxylate, and furan (1 to 6 mole) are introduced into an autoclave, and the mixture is reacted at a temperature of 130 to 150° C. and a pressure of 10 to 30 atm for 10 hours. After the reaction is completed, the reaction mixture is distilled in vacuo to obtain the compound represented by the following Chemical Formula 115:

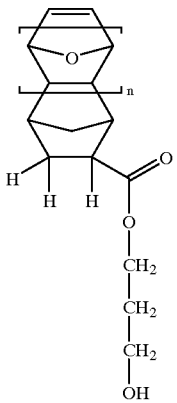

Chemical Formula 115

The value 'n' changes depending on the amount of furan introduced; i.e. the 'n' value of the final product approximately increases by 1 with every 1.2 mole increase of furan.

EXAMPLE 16

The procedure of Example 15 is repeated but using thiophene (1 to 6 mole) instead of furan (1 to 6 mole), to obtain the compound of the following Chemical Formula 116:

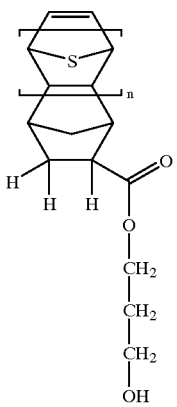

Chemical Formula 116

EXAMPLE 17

Tetrahydrofuran solvent (500 g), tert-butyl acrylate (1.2 mole) of Chemical Formula 3c below, and thiophene (1.0 mole) are introduced into a 2-liter flask, and the mixture is stirred at 70° C. for 24 hours. After the reaction is completed, the solvent and excess amount of tert-butyl acrylate are removed by using a rotary evaporator. The residue is distilled in vacuo to obtain pure tert-butyl 7-thiabicyclo[2.2.1]hept-5-ene-2-carboxylate represented by Chemical Formula 117 below (yield: 80%).

Chemical Formula 3c

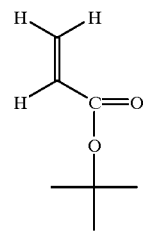

Chemical Formula 117

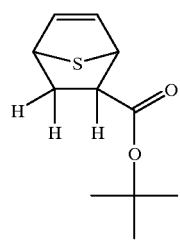

EXAMPLE 18

The procedure of Example 17 is repeated but using furan (1 mole) instead of thiophene (1.0 mole), to obtain pure 1,1-dimethylethyl 7-oxabicyclo[2.2.1]hept-5-ene-2-carboxylate (yield: 85%) of the following Chemical Formula 118:

Chemical Formula 118

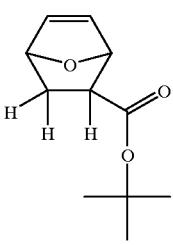

EXAMPLE 19

Tetrahydrofuran solvent (500 g), the compound of Chemical Formula 117 obtained from Example 17 (that is, tert-butyl 7-thiabicyclo[2.2.1]hept-5-ene-2-carboxylate, 1 mole), and furan (1 to 6 mole) are introduced into an autoclave, and the mixture is reacted at a temperature of 130 to 1500° C. and a pressure of 10 to 30 atm for 10 hours, to obtain the compound represented by the following Chemical Formula 119.<

Chemical Formula 119

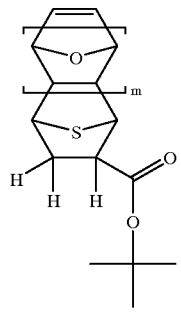

The value 'm' changes depending on the amount of furan introduced; i.e. the 'm' value approximately increases by 1 with every 1.2 mole increase of furan.

EXAMPLE 20

The procedure of Example 19 is repeated but using 1,1-dimethylethyl 7-oxabicyclo[2.2.1]hept-5-ene-2-carboxylate (1 mole) instead of 1,1-dimethylethyl 7-thiabicyclo[2.2.1]hept-5-ene-2-carboxylate (1 mole), and thiophene (1 to 6 mole) instead of furan (1 to 6 mole), to obtain the compound of the following Chemical Formula 120:

Chemical Formula 120

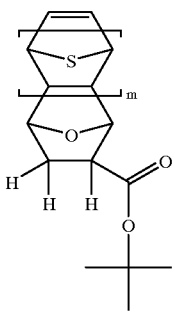

EXAMPLE 21

The procedure of Example 19 is repeated but using thiophene (1 to 6 mole) instead of furan (1 to 6 mole), to obtain the compound of the following Chemical Formula 121:

Chemical Formula 121

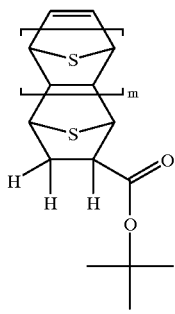

EXAMPLE 22

The procedure of Example 19 is repeated but using 1,1-dimethylethyl 7-oxabicyclo[2.2.1]hept-5-ene-2-carboxylate (1 mole) instead of 1,1-dimethylethyl 7-thiabicyclo[2.2.1]hept-5-ene-2-carboxylate (1 mole), to obtain the compound of the following Chemical Formula 122:

Chemical Formula 122

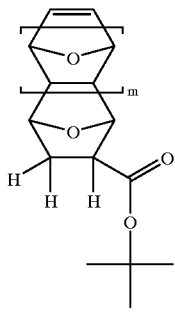

EXAMPLE 23

A solution of 1,1-dimethylethyl bicyclo[2.2.1]hept-5-ene-2-carboxylate and furan (1 to 6 mole) in tetrahydrofuran solvent (500 g) are introduced into an autoclave, and the solution is reacted at a temperature of 130 to 1500° C. and a pressure of 10 to 30 atm for 10 hours, to obtain the compound represented by Chemical Formula 25. After the reaction is completed, the reaction mixture is distilled in vacuo to obtain the compound represented by the following Chemical Formula 123:

Chemical Formula 123

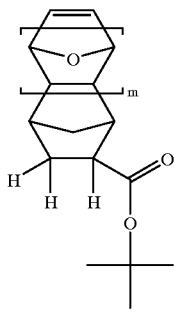

The value 'm' changes depending on the amount of furan introduced; i.e. the 'm' value approximately increases by 1 with every 1.2 mole increase of furan.

EXAMPLE 24

The procedure of Example 23 is repeated but using thiophene (1 to 6 mole) instead of furan (1 to 6 mole), to obtain the compound of the following Chemical Formula 124:

Chemical Formula 124

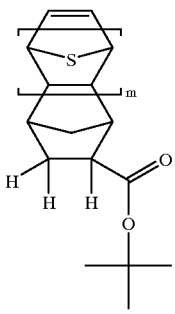

EXAMPLE 25

In tetrahydrofuran solvent (500 g), tert-butyl methacrylate (1.2 mole) of Chemical Formula 3d below and thiophene (1.0 mole) are dissolved, and the solution is introduced into a 2-liter flask. After stirring at 700° C., 10 atm for 24 hours, the solvent and excess amount of tert-butyl methacrylate are removed by using a rotary evaporator. The residue is distilled in vacuo to obtain pure 1,1-dimethylethyl 2-methyl-7-thiabicyclo[2.2.1]hept-5-ene-2-carboxylate of Chemical Formula 125 (yield: 50%).

Chemical Formula 3d

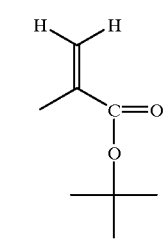

Chemical Formula 125

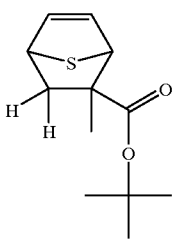

EXAMPLE 26

The procedure of Example 25 is repeated but using furan (1 mole) instead of thiophene (1.0 mole), to obtain pure 1,1-dimethylethyl 2-methyl-7-oxabicyclo[2.2.1]hept-5-ene-2-carboxylate (yield: 45%) of Chemical Formula 126:

Chemical Formula 126

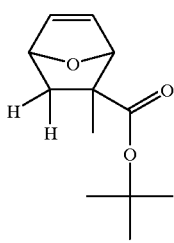

EXAMPLE 27

A solution of 1,1-dimethylethyl 2-methyl-7-thiabicyclo[2.2.1]hept-5-ene-2-carboxylate (1 mole) of Chemical Formula 125 obtained from Example 25, and furan (1 to 6 mole) in tetrahydrofuran solvent (500 g) is introduced into an autoclave, and the solution is reacted at a temperature of 130 to 1500° C. and a pressure of 10 to 30 atm for 10 hours, to obtain the compound represented by Chemical Formula 127.

Chemical Formula 127

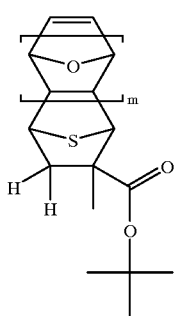

The value 'm' changes depending on the amount of furan introduced; i.e. the 'm' value of the final product approximately increases by 1 with every 1.2 mole increase of furan.

EXAMPLE 28

The procedure of Example 27 is repeated but using 1,1-dimethylethyl 2-methyl-7-oxabicyclo[2.2.1]hept-5-ene-2-carboxylate instead of 1,1-dimethylethyl 2-methyl-7-thiabicyclo[2.2.1]hept-5-ene-2-carboxylate (1 mole), and thiophene (1 to 6 mole) instead of furan (1 to 6 mole), to obtain the compound of the following Chemical Formula 128:

Chemical Formula 128

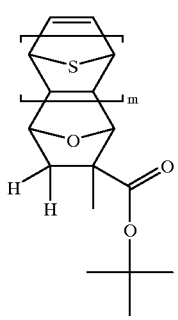

EXAMPLE 29

The procedure of Example 27 is repeated but using thiophene (1 to 6 mole) instead of furan (1 to 6 mole), to obtain the compound of the following Chemical Formula 129:

Chemical Formula 129

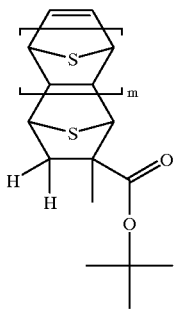

EXAMPLE 30

The procedure of Example 27 is repeated but using 1,1-dimethylethyl 2-methyl-7-oxabicyclo[2.2.1]hept-5-ene-2-carboxylate instead of 1,1-dimethylethyl 2-methyl-7-thiabicyclo[2.2.1]hept-5-ene-2-carboxylate (1 mole), to obtain the compound of the following Chemical Formula 130:

Chemical Formula 130

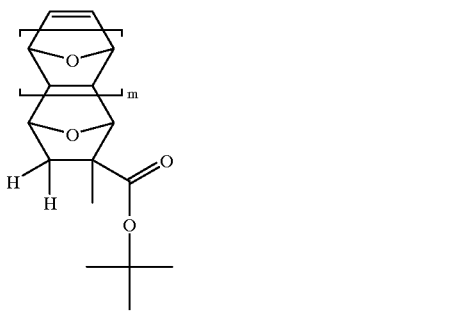

EXAMPLE 31

A solution of 1,1-dimethylethyl 2-methylbicyclo[2.2.1]hept-5-ene-2-carboxylate (1 mole) and furan (1 to 6 mole) in tetrahydrofuran solvent (500 g) is introduced into an autoclave, and the solution is reacted at a temperature of 130 to 1500° C. and a pressure of 10 to 30 atm for 10 hours. The value 'm' changes depending on the amount of furan introduced; 'm' value approximately increases by 1 with increase of every 1.2 mole of furan. After the reaction is completed, the residue is distilled in vacuo to obtain the compound represented by the following Chemical Formula 131:

Chemical Formula 131

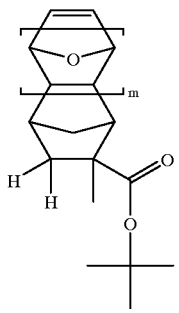

EXAMPLE 32

The procedure of Example 31 is repeated but using thiophene (1 to 6 mole) instead of furan (1 to 6 mole), to obtain the compound of the following Chemical Formula 132:

Chemical Formula 132

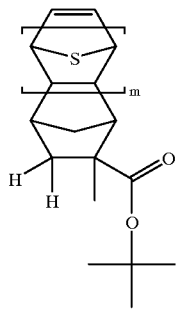

EXAMPLE 33

In tetrahydrofuran solvent (500 g), thiophene (1 mole) and maleic anhydride (1 mole) are dissolved, and the solution is introduced into a 2-liter flask. After stirring at 700° C. for 24 hours, the solvent is removed by using a rotary evaporator. The residue is distilled in vacuo to obtain pure 7-thiabicyclo[2.2.1]hept-5-ene-2,3-dicarboxylic anhydride of the following Chemical Formula 201 (yield: 90%).

Chemical Formula 201

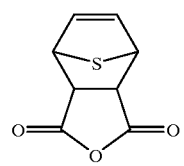

The compound of Chemical Formula 201 (7-thiabicyclo [2.2.1]hept-5-ene-2,3-dicarboxylic anhydride) (50 g) thus prepared is well mixed with tetrahydrofuran (200 ml), and tert-butanol (50 g) is added thereto. After adding 1 g of hydrochloric acid, the resultant mixture is heated under reflux at 700° C. for 20 hours. When the reaction mixture is cooled to room temperature, crystals are formed. The obtained crystals are dried in vacuo, to give 1,1-dimethylethyl 7-thiabicyclo[2.2.1]hept-5-ene-2,3-dicarboxylic acid of the following Chemical Formula 133 (yield: 70%).

Chemical Formula 133

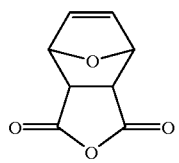

EXAMPLE 34

The procedure of Example 33 is repeated but using furan instead of thiophene, to obtain 7-oxabicyclo[2.2.1]hept-5-ene-2,3-dicarboxylic anhydride of the following Chemical Formula 202 (yield: 90%).

Chemical Formula 202

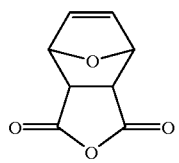

The procedure of Example 33 is repeated but using 7-oxabicyclo[2.2.1]hept-5-ene-2,3-dicarboxylic anhydride of Chemical Formula 202 instead of 7-thiabicyclo[2.2.1] hept-5-ene-2,3-dicarboxylic anhydride of Chemical Formula 201, to obtain 1,1-dimethylethyl 7-oxabicyclo[2.2.1] hept-5-ene-2,3-dicarboxylic acid of Chemical Formula 134 (yield: 72%).

Chemical Formula 134

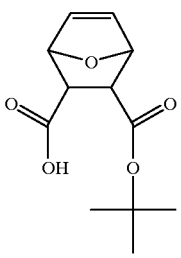

EXAMPLE 35

The procedure of Example 33 is repeated but using cyclopentadiene instead of thiophene, to obtain bicyclo [2.2.1]hept-5-ene-2,3-dicarboxylic anhydride of Chemical Formula 203 (yield: 90%).

Chemical Formula 203

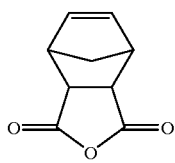

The procedure of Example 33 is repeated but using bicyclo[2.2.1]hept-5-ene-2,3-dicarboxylic anhydride of Chemical Formula 203 instead of 7-thiabicyclo[2.2.1]hept-5-ene-2,3-dicarboxylic anhydride of Chemical Formula 201, to obtain 1,1-dimethylethyl bicyclo[2.2.1]hept-5-ene-2,3-dicarboxylic acid of Chemical Formula 135 (yield: 70%).

Chemical Formula 135

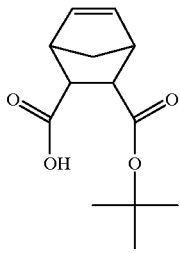

EXAMPLE 36

Tetrahydrofuran solvent (300 g), 7-thiabicyclo[2.2.1]hept-5-ene-2,3-dicarboxylic anhydride (1 mole) and furan (1 to 6 mole) are introduced into an autoclave, and the mixture is reacted at a temperature of 130 to 1500° C. and a pressure of 10 to 30 atm for 10 hours. After the reaction is completed, the residue is distilled in vacuo to obtain the compound represented by Chemical Formula 204.

Chemical Formula 204

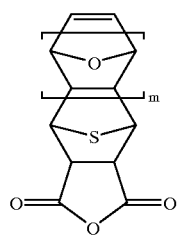

The value 'm' changes depending on the amount of furan introduced; i.e. the 'm' value of the final product approximately increases by 1 with every 1.2 mole increase of furan.

The compound of Chemical Formula 204 (50 g) thus prepared is well mixed with tetrahydrofuran (200 ml), and tert-butanol (50 g) is added thereto. After adding 1 g of hydrochloric acid, the resultant mixture is heated under reflux at 700° C. for 20 hours. When the reaction mixture is cooled to room temperature, crystals are formed. The obtained crystals are dried in vacuo, to obtain the compound of Chemical Formula 136.

Chemical Formula 136

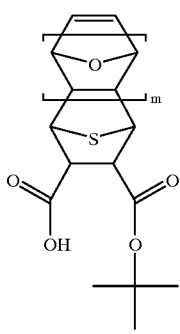

EXAMPLE 37

The procedure of Example 36 is repeated but using the compound of Chemical Formula 205, which is prepared by using 7-oxabicyclo[2.2.1]hept-5-ene-2,3-dicarboxylic anhydride of Chemical Formula 202 instead of 7-thiabicyclo[2.2.1]hept-5-ene-2,3-dicarboxylic anhydride of Chemical Formula 201, and thiophene instead of furan, to obtain the compound of Chemical Formula 137.

Chemical Formula 205

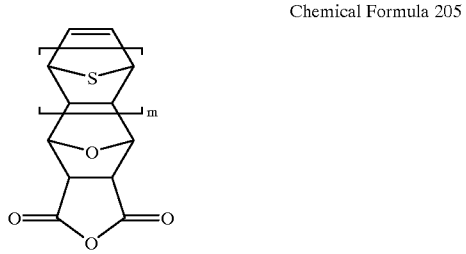

Chemical Formula 137

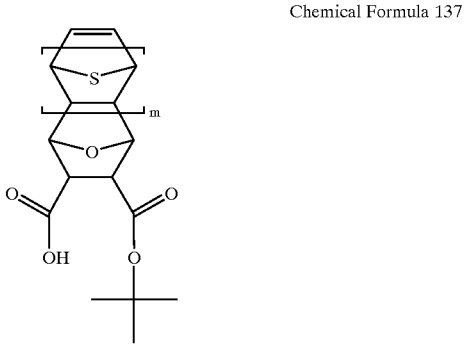

EXAMPLE 38

The procedure of Example 36 is repeated but using the compound of Chemical Formula 206, which is prepared by using thiophene instead of furan, to obtain the compound of Chemical Formula 138.

Chemical Formula 206

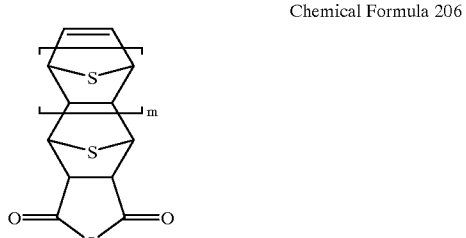

Chemical Formula 138

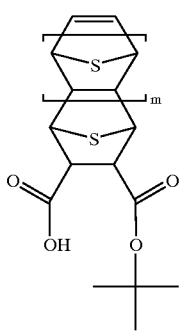

EXAMPLE 39

The procedure of Example 36 is repeated but using the compound of Chemical Formula 207, which is prepared by using 7-oxabicyclo[2.2.1]hept-5ene-2,3-dicarboxylic anhydride of Chemical Formula 202 instead of 7-thiabicyclo[2.2.1]hept-5-ene-2,3-dicarboxylic anhydride of Chemical Formula 201, to obtain the compound of Chemical Formula 139.

Chemical Formula 207

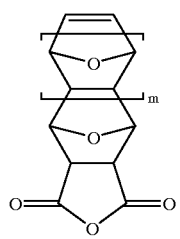

Chemical Formula 139

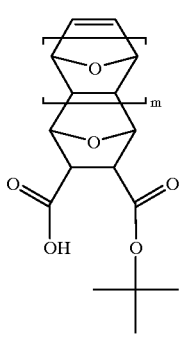

EXAMPLE 40

The procedure of Example 36 is repeated but using the compound of Chemical Formula 208, which is prepared by using bicyclo[2.2.1]hept-5-ene-2,3-dicarboxylic anhydride of Chemical Formula 203 instead of 7-thiabicyclo[2.2.1]hept-5-ene-2,3-dicarboxylic anhydride of Chemical Formula 201, to obtain the compound of Chemical Formula 140.

Chemical Formula 208

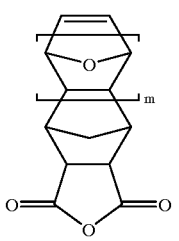

Chemical Formula 140

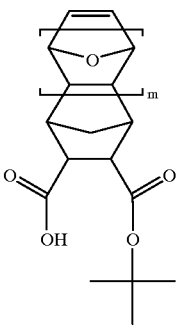

EXAMPLE 41

The procedure of Example 36 is repeated but using the compound of Chemical Formula 209, which is prepared by using bicyclo[2.2.1]hept-5-ene-2,3-dicarboxylic anhydride of Chemical Formula 203 instead of 7-thiabicyclo[2.2.1]hept-5-ene-2,3-dicarboxylic anhydride of Chemical Formula 201, and thiophene instead of furan, to obtain the compound of Chemical Formula 141.

Chemical Formula 209

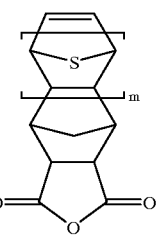

Chemical Formula 141

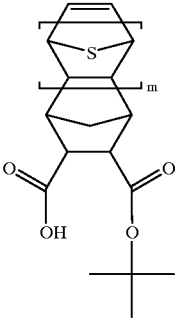

EXAMPLE 42

Tetrahydrofuran solvent (500 g), acrylic acid (1.2 mole) and thiophene (1.0 mole) are introduced into a 2-liter flask. After stirring at 700° C. for 24 hours, the solvent and excessive acrylic acid are removed by using a rotary evaporator. The residue is distilled in vacuo to obtain pure 7-thiabicyclo[2.2.1]hept-5-ene-2-carboxylic acid of Chemical Formula 142 (yield: 80%).

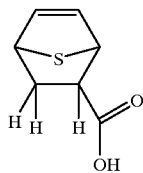

Chemical Formula 142

EXAMPLE 43

The procedure of Example 42 is repeated but using furan (1 mole) instead of thiophene (1.0 mole), to obtain pure 7-oxabicyclo[2.2.1]hept-5-ene-2-carboxylic acid of Chemical Formula 143 (yield: 80%).

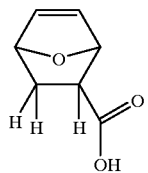

Chemical Formula 143

EXAMPLE 44

Tetrahydrofuran solvent (500 g), pure 7-thiabicyclo[2.2.1]hept-5-ene-2-carboxylic acid (1 mole) and furan (1 to 6 mole) are introduced to an autoclave, and the mixture is reacted at a temperature of 130 to 1500° C. and a pressure of 10 to 30 atm for 10 hours. After the reaction is completed, the residue is distilled in vacuo to obtain the compound represented by the following Chemical Formula 144.

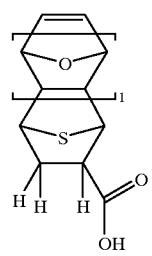

Chemical Formula 144

The value 'l' changes depending on the amount of furan introduced; i.e. the 'l' value of the final product approximately increases by 1 with every 1.2 mole increase of furan.

EXAMPLE 45

The procedure of Example 42 is repeated but using 7-oxabicyclo[2.2.1]hept-5-ene-2-carboxylic acid (1 mole) instead of 7-thiabicyclo[2.2.1]hept-5-ene-2-carboxylic acid (1 mole), and thiophene (1 to 6 mole) instead of furan (1 to 6 mole), to obtain the compound of Chemical Formula 145.

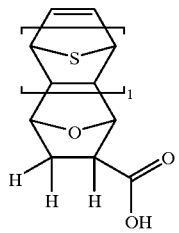

Chemical Formula 145

EXAMPLE 46

The procedure of Example 44 is repeated but using thiophene (1 to 6 mole) instead of furan (1 to 6 mole), to obtain the compound of Chemical Formula 146.

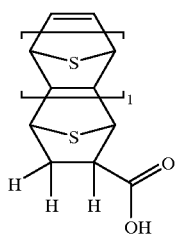

Chemical Formula 146

EXAMPLE 47

The procedure of Example 44 is repeated but using 7-oxabicyclo[2.2.1]hept-5-ene-2-carboxylic acid instead of 7-thiabicyclo[2.2.1]hept-5-ene-2-carboxylic acid (1 mole), to obtain the compound represented by the following Chemical Formula 147:

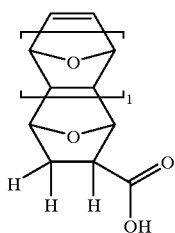

Chemical Formula 147

EXAMPLE 48

Tetrahydrofuran solvent (500 g), bicyclo[2.2.1]hept-5-ene-2-carboxylic acid and furan (1 to 6 mole) are introduced into an autoclave, and the mixture is reacted at a temperature of 130 to 1500° C. and a pressure of 10 to 30 atm for 10 hours. After the reaction is completed, the residue is distilled in vacuo to obtain the compound represented by the following Chemical Formula 148.

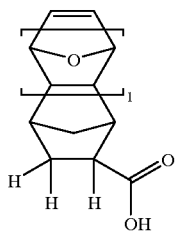

Chemical Formula 148

The value 'l' changes depending on the amount of furan introduced; i.e. the 'l' value of the final product approximately increases by 1 with every 1.2 mole increase of furan.

EXAMPLE 49

The procedure of Example 48 is repeated but using thiophene (1 to 6 mole) instead of furan (1 to 6 mole), to obtain the compound represented by the following Chemical Formula 149:

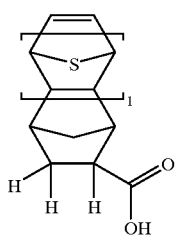

Chemical Formula 149

EXAMPLE 50

Tetrahydrofuran solvent (500 g), methacrylic acid (1.2 mole) and thiophene (1.0 mole) are introduced into a 2-liter flask. After stirring at 700° C. for 24 hours, the solvent and excessive methacrylic acid are removed by using a rotary evaporator. The residue is distilled in vacuo to obtain pure 2-methyl-7-thiabicyclo[2.2.1]hept-5-ene-2-carboxylic acid of Chemical Formula 150 (yield: 50%).

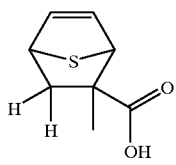

Chemical Formula 150

EXAMPLE 51

The procedure of Example 50 is repeated but using furan (1 mole) instead of thiophene (1.0 mole), to obtain pure 2-methyl-7-oxabicyclo[2.2.1]hept-5-ene-2-carboxylic acid of Chemical Formula 151 (yield: 80%).

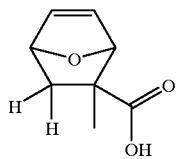

Chemical Formula 151

EXAMPLE 52

Tetrahydrofuran solvent (500 g), 2-methyl-7-thiabicyclo [2.2.1]hept-5-ene-2-carboxylic acid (1 mole) of Chemical Formula 150 obtained from Example 50 and furan (1 to 6 mole) are introduced into an autoclave, and the mixture is reacted at a temperature of 130 to 1500° C. and a pressure of 10 to 30 atm for 10 hours. After the reaction is completed, the residue is distilled in vacuo to obtain the compound represented by the following Chemical Formula 152:

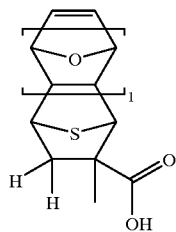

Chemical Formula 152

The value 'l' changes depending on the amount of furan introduced; i.e. the 'l' value of the final product approximately increases by 1 with every 1.2 mole increase of furan.

EXAMPLE 53

The procedure of Example 52 is repeated but using 2-methyl-7-oxabicyclo[2.2.1]hept-5-ene-2-carboxylic acid (1 mole) instead of 2-methyl-7-thiabicyclo[2.2.1]hept-5-ene-2-carboxylic acid (1 mole), and thiophene (1 to 6 mole) instead of furan (1 to 6 mole), to obtain the compound represented by the following Chemical Formula 153:

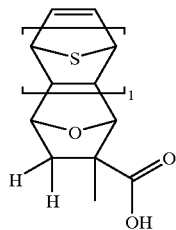

Chemical Formula 153

EXAMPLE 54

The procedure of Example 52 is repeated but using thiophene (1 to 6 mole) instead of furan (1 to 6 mole), to obtain the compound represented by the following Chemical Formula 154:

Chemical Formula 154

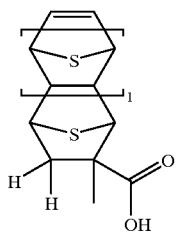

EXAMPLE 55

The procedure of Example 52 is repeated but using 2-methyl-7-oxabicyclo[2.2.1]hept-5-ene-2-carboxylic acid instead of 2-methyl-7-thiabicyclo[2.2.1]hept-5-ene-2-carboxylic acid (1 mole), to obtain the compound represented by the following Chemical Formula 155:

Chemical Formula 155

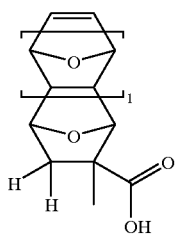

EXAMPLE 56

Tetrahydrofuran solvent (500 g), 2-methylbicyclo[2.2.1]hept-5-ene-2-carboxylic acid and furan (1 to 6 mole) are introduced into an autoclave, and the mixture is reacted at a temperature of 130 to 1500° C. and a pressure of 10 to 30 atm for 10 hours. After the reaction is completed, the residue is distilled in vacuo to obtain the compound represented by the following Chemical Formula 156:

Chemical Formula 156

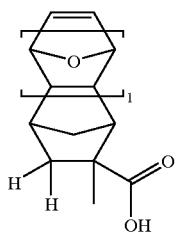

The value 'l' changes depending on the amount of furan introduced; i.e. the 'l' value of the final product approximately increases by 1 with every 1.2 mole increase of furan.

EXAMPLE 57

The procedure of Example 56 is repeated but using thiophene (1 to 6 mole) instead of furan (1 to 6 mole), to obtain the compound represented by the following Chemical Formula 157:

Chemical Formula 157

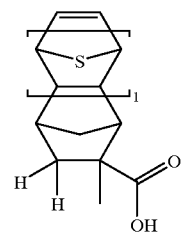

EXAMPLE 58

The compound of Chemical Formula 201, that is, 7-thiabicyclo[2.2.1]hept-5-ene-2,3-dicarboxylic anhydride (50 g) is well mixed with tetrahydrofuran (200 ml), and methanol (50 g) is added thereto. After adding 1 g of hydrochloric acid thereto, the resultant mixture is heated under reflux at 700° C. for 20 hours. Upon cooling the mixture to room temperature, crystals are formed. The crystals are dried in vacuo to obtain methyl 7-thiabicyclo[2.2.1]hept-5-ene-2,3-dicarboxylic acid of Chemical Formula 158 (yield: 70%).

Chemical Formula 158

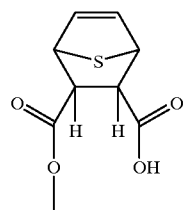

EXAMPLE 59

The procedure of Example 58 is repeated but using 7-oxabicyclo[2.2.1]hept-5-ene-2,3-dicarboxylic anhydride of Chemical Formula 202 instead of 7-thiabicyclo[2.2.1]hept-5-ene-2,3-dicarboxylic anhydride of Chemical Formula 201, to obtain methyl 7-oxabicyclo[2.2.1]hept-5-ene-2,3-dicarboxylic acid represented by Chemical Formula 159 (yield: 76%).

Chemical Formula 159

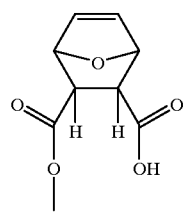

EXAMPLE 60

The procedure of Example 58 is repeated but using bicyclo[2.2.1]hept-5-ene-2,3-dicarboxylic anhydride of Chemical Formula 203 instead of 7-thiabicyclo[2.2.1]hept-5-ene-2,3-dicarboxylic anhydride of Chemical Formula 201, to obtain methyl bicyclo[2.2.1]hept-5-ene-2,3-dicarboxylic acid represented by Chemical Formula 160 (yield: 78%).

Chemical Formula 160

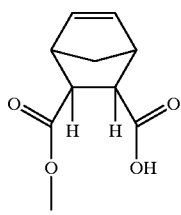

EXAMPLE 61

<1>Method 1:

Tetrahydrofuran solvent (500 g), methyl 7-thiabicyclo[2.2.1]hept-5-ene-2,3-dicarboxylic acid and furan (1 to 6 mole) are introduced into an autoclave, and the mixture is reacted at a temperature of 130 to 1500° C. and a pressure of 10 to 30 atm for 10 hours. After the reaction is completed, the residue is distilled in vacuo to obtain the compound represented by Chemical Formula 161.

Chemical Formula 161

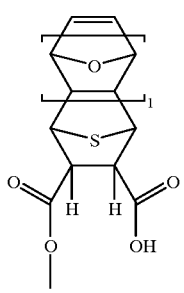

The value 'l' changes depending on the amount of furan introduced; i.e. the 'l' value of the final product approximately increases by 1 with every 1.2 mole increase of furan.

Instead of distillation in vacuo, the product may be isolated by recrystallization from ethyl ether. However, recrystallization may be applied only to the cases when l is 1, 2, 3, 4 or 5.

<2> Method 2:

The compound of Chemical Formula 204 obtained from Example 35 is well mixed with tetrahydrofuran (200 ml), and methanol (50 g) is added thereto. After adding 1 g of hydrochloric acid thereto, the resultant mixture is heated under reflux at 700° C. for 20 hours. Upon cooling the mixture to room temperature, crystals are formed. The crystals are dried in vacuo to obtain the compound of Chemical Formula 161.

EXAMPLE 62

<1> Method 1:

The procedure according to Example 61 is repeated but using methyl 7-oxabicyclo[2.2.1]hept-5-ene-2,3-dicarboxylic acid of Chemical Formula 59 instead of methyl 7-thiabicyclo[2.2.1]hept-5-ene-2,3-dicarboxylic acid of Chemical Formula 58, and thiophene instead of furan, to obtain the compound represented by the following Chemical Formula 162:

Chemical Formula 162

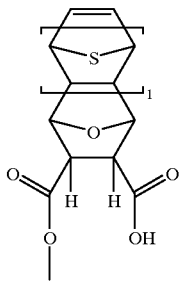

<2> Method 2:

The compound (50 g) is well mixed with tetrahydrofuran (200 ml), and methanol (50 g) is added thereto. After adding 1 g of hydrochloric acid thereto, the resultant mixture is heated under reflux at 700° C. for 20 hours. Upon cooling the mixture to room temperature, crystals are formed. The crystals are dried in vacuo to obtain the compound of Chemical Formula 162.

<3> Method 3:

The procedure according to Method 2 of Example 61 is repeated but using the same amount of the compound of Chemical Formula 205 obtained from Example 36, instead of the compound of Chemical Formula 204 obtained from Example 35, to obtain the compound represented by above Chemical Formula 162.

EXAMPLE 63

<1> Method 1:

The procedure according to Example 61 is repeated but using thiophene instead of furan, to obtain the compound represented by the following Chemical Formula 163:

Chemical Formula 163

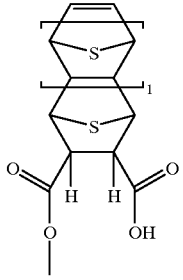

<2> Method 2:

The procedure according to Method 2 of Example 61 is repeated but using the same amount of the compound of Chemical Formula 206 obtained from Example 37, instead of the compound of Chemical Formula 204 obtained from Example 35, to obtain the compound represented by above Chemical Formula 163.

EXAMPLE 64

<1> Method 1:

The procedure according to Example 61 is repeated but using methyl 7-oxabicyclo[2.2.1]hept-5-ene-2,3-dicarboxylic acid of Chemical Formula 59 instead of methyl 7-thiabicyclo[2.2.1]hept-5-ene-2,3-dicarboxylic acid of Chemical Formula 58, to obtain the compound represented by the following Chemical Formula 164:

Chemical Formula 164

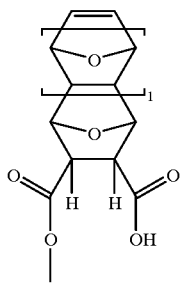

<2> Method 2:

The procedure according to Method 2 of Example 61 is repeated but using the same amount of the compound of Chemical Formula 207 obtained from Example 38, instead of the compound of Chemical Formula 204 obtained from Example 35, to obtain the compound represented by above Chemical Formula 164.

EXAMPLE 65

<1> Method 1:

The procedure according to Example 61 is repeated but using methyl bicyclo[2.2.1]hept-5-ene-2,3-dicarboxylic acid of Chemical Formula 59 instead of methyl 7-thiabicyclo[2.2.1]hept-5-ene-2,3-dicarboxylic acid of Chemical Formula 58, to obtain the compound represented by the following Chemical Formula 165:

Chemical Formula 165

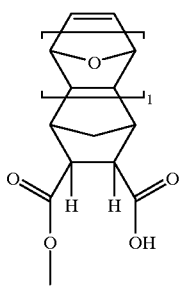

<2> Method 2:

The procedure according to Method 2 of Example 61 is repeated but using the same amount of the compound of Chemical Formula 207 obtained from Example 38, instead of the compound of Chemical Formula 204 obtained from Example 35, to obtain the compound represented by above Chemical Formula 165.

EXAMPLE 66

<1> Method 1:

The procedure according to Example 61 is repeated but using methyl bicyclo[2.2.1]hept-5-ene-2,3-dicarboxylic acid of Chemical Formula 59 instead of methyl 7-thiabicyclo[2.2.1]hept-5-ene-2,3-dicarboxylic acid of Chemical Formula 58, to obtain the compound represented by the following Chemical Formula 166:

Chemical Formula 166

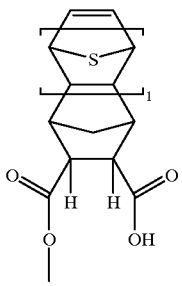

<2> Method 2:

The procedure according to Method 2 of Example 61 is repeated but using the same amount of the compound of Chemical Formula 208 obtained from Example 39, instead of the compound of Chemical Formula 204 obtained from Example 35, to obtain the compound represented by above Chemical Formula 166.

EXAMPLE 67

The compound of Chemical Formula 201, that is 7-thiabicyclo[2.2.1]hept-5ene-2,3-dicarboxylic anhydride (50 g) is well mixed with water (200 ml), and 1 g of hydrochloric acid is added thereto. The resultant mixture is heated under reflux at 700° C. for 20 hours. Upon cooling the mixture to room temperature, crystals are formed. The crystals are dried in vacuo to obtain 7-thiabicyclo[2.2.1]hept-5-ene-2,3-dicarboxylic acid represented by Chemical Formula 167 (yield: 70%).

Chemical Formula 167

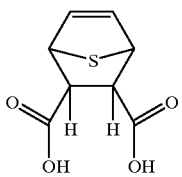

EXAMPLE 68

The procedure according to Example 67 is repeated but using 7-oxabicyclo[2.2.1]hept-5-ene-2,3-dicarboxylic anhydride of Chemical Formula 202 instead of 7-thiabicyclo [2.2.1]hept-5-ene-2,3-dicarboxylic acid of Chemical Formula 201, to obtain 7-oxabicyclo[2.2.1]hept-5-ene-2,3-dicarboxylic acid represented by Chemical Formula 168 (yield: 72%).

Chemical Formula 168

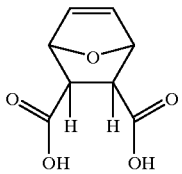

EXAMPLE 69

The procedure according to Example 67 is repeated but using bicyclo[2.2.1]hept-5-ene-2,3-dicarboxylic anhydride of Chemical Formula 202 instead of 7-thiabicyclo[2.2.1]hept-5-ene-2,3-dicarboxylic acid of Chemical Formula 201, to obtain bicyclo[2.2.1]hept-5-ene-2,3-dicarboxylic acid represented by Chemical Formula 169 (yield: 72%).

Chemical Formula 169

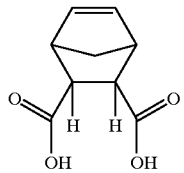

EXAMPLE 70

<1> Method 1:

Tetrahydrofuran solvent (500 g), 7thiabicyclo[2.2.1l]hept-5-ene-2,3-dicarboxylic acid of Chemical Formula 201 and furan (1 to 6 mole) are introduced into an autoclave, and the mixture is reacted at a temperature of 130 to 1500° C. and a pressure of 10 to 30 atm for 10 hours. After the reaction is completed, the residue is distilled in vacuo to obtain the compound represented by Chemical Formula 170.

Chemical Formula 170

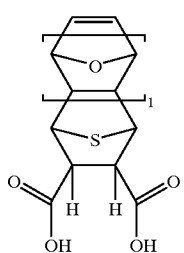

The value '1' changes depending on the amount of furan introduced; i.e. the '1' value of the final product approximately increases by 1 with every 1.2 mole increase of furan.

Instead of distillation in vacuo, the product may be isolated by recrystallization from ethyl ether. However, recrystallization may be applied only to the cases when 1 is 1, 2, 3, 4 or 5.

<2> Method 2:

The compound of Chemical Formula 204 (50 g) is well mixed with water (200 ml), and 1 g of hydrochloric acid is thereto. The resultant mixture is heated under reflux at 700° C. for 20 hours. Upon cooling the mixture to room temperature, crystals are formed. The crystals are dried in vacuo to obtain the compound of above Chemical Formula 170.

EXAMPLE 71

<1> Method 1:

The procedure according to Example 70 is repeated but using 7-oxabicyclo[2.2.1]hept-5-ene-2,3-dicarboxylic acid of Chemical Formula 202 instead of 7-thiabicyclo[2.2.1]hept-5-ene-2,3-dicarboxylic acid of Chemical Formula 201, and thiophene instead of furan, to obtain the compound represented by the following Chemical Formula 171:

Chemical Formula 171

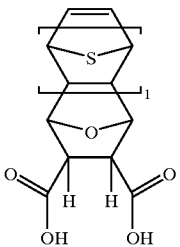

<2> Method 2:

The procedure according to Method 2 of Example 70 is repeated but using the compound of Chemical Formula 205 instead of the compound of Chemical Formula 204, to obtain the compound represented by above Chemical Formula 171.

EXAMPLE 72

<1 > Method 1:

The procedure according to Example 70 is repeated but using thiophene instead of furan, to obtain the compound represented by the following Chemical Formula 172:

Chemical Formula 172

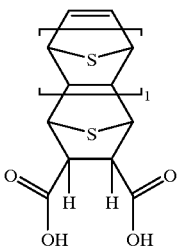

<2> Method 2:

The procedure according to Method 2 of Example 70 is repeated but using the compound of Chemical Formula 206 instead of the compound of Chemical Formula 204, to obtain the compound represented by above Chemical Formula 172.

EXAMPLE 73

<1> Method 1:

The procedure according to Example 70 is repeated but using 7-oxabicyclo[2.2.1]hept-5-ene-2,3-dicarboxylic acid of Chemical Formula 202 instead of 7-thiabicyclo[2.2.1]hept-5-ene-2,3-dicarboxylic acid of Chemical Formula 201, to obtain the compound represented by the following Chemical Formula 173:

Chemical Formula 173

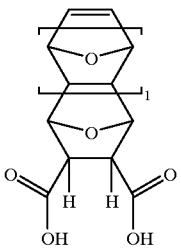

<2> Method 2:

The procedure according to Method 2 of Example 70 is repeated but using the compound of Chemical Formula 207 instead of the compound of Chemical Formula 204, to obtain the compound represented by above Chemical Formula 173.

EXAMPLE 74

<1> Method 1:

The procedure according to Example 70 is repeated but using bicyclo[2.2.1]hept-5-ene-2,3-dicarboxylic acid of Chemical Formula 202 instead of 7-thiabicyclo[2.2.1]hept-5-ene-2,3-dicarboxylic acid of Chemical Formula 201, to obtain the compound represented by the following Chemical Formula 174:

Chemical Formula 174

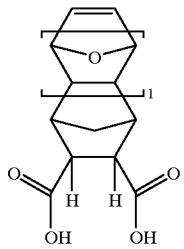

<2> Method 2:

The procedure according to Method 2 of Example 70 is repeated but using the compound of Chemical Formula 208 instead of the compound of Chemical Formula 204, to obtain the compound represented by above Chemical Formula 174.

EXAMPLE 75

<1> Method 1:

The procedure according to Example 70 is repeated but using bicyclo[2.2.1]hept-5-ene-2,3-dicarboxylic acid of Chemical Formula 202 instead of 7-thiabicyclo[2.2.1]hept-5-ene-2,3-dicarboxylic acid of Chemical Formula 201, and thiophene instead of furan, to obtain the compound represented by the following Chemical Formula 175:

Chemical Formula 175

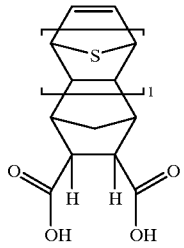

<2> Method 2:

The procedure according to Method 2 of Example 70 is repeated but using the compound of Chemical Formula 209 instead of the compound of Chemical Formula 204, to obtain the compound represented by above Chemical Formula 175.

EXAMPLE 76

In tetrahydrofuran solvent, dissolved are (i) 1,1-dimethylethyl 12-oxatetracyclo[4.4.0.1.1]dodec-7-ene-2-carboxylate (0.8 mole) as the first comonomer, (ii) 2-hydroxyethyl 12-oxatetracyclo[4.4.0.1.1]dodec-7-ene-2-carboxylate (0.15 mole) as the second comonomer, (iii) 12-oxatetracyclo[4.4.0.1.1]dodec-7-ene-2-carboxylic acid (0.05 mole) as the third comonomer, and (iv) maleic anhydride (1.0 mole) as the polymerization-enhancing comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/2-hydroxyethyl 12-oxatetracyclo[4.4.0.1.1]dodec-7-ene-2-carboxylate/maleic anhydride) represented by the following Chemical Formula 176:

Chemical Formula 176

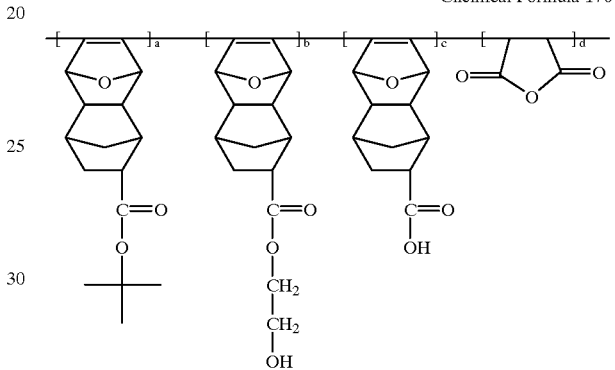

EXAMPLE 77

The procedure according to Example 76 is repeated but using 11,12-dioxatetracyclo[4.4.0.1.1]dodec-7-ene-2-carboxylic acid (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/11,12-dioxatetracyclo[4.4.0.1.1]dodec-7-ene-2-carboxylic acid/2-hydroxyethyl 12-oxatetracyclo[4.4.0.1.1]dodec-7-ene-2-carboxylate/maleic anhydride) represented by the following Chemical Formula 177:

Chemical Formula 177

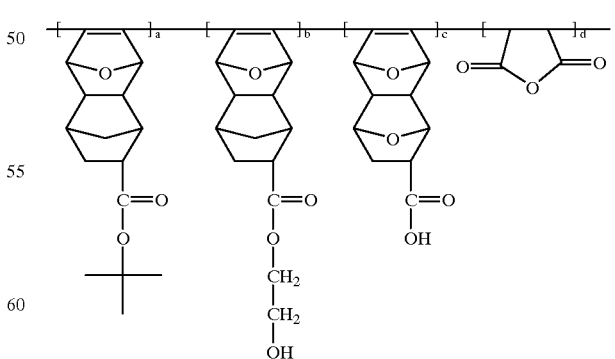

EXAMPLE 78

The procedure according to Example 76 is repeated but using 11,12-dithiatetracyclo[4.4.0.1.1]dodec-7-ene-2- carboxylic acid (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/11,12-dithiatetracyclo[4.4.0.1.1]dodec-7-ene-2-carboxylic acid/2-hydroxyethyl 12-oxatetracyclo[4.4.0.1.1]dodec-7-ene-2-carboxylate/maleic anhydride) represented by the following Chemical Formula 178:

Chemical Formula 178

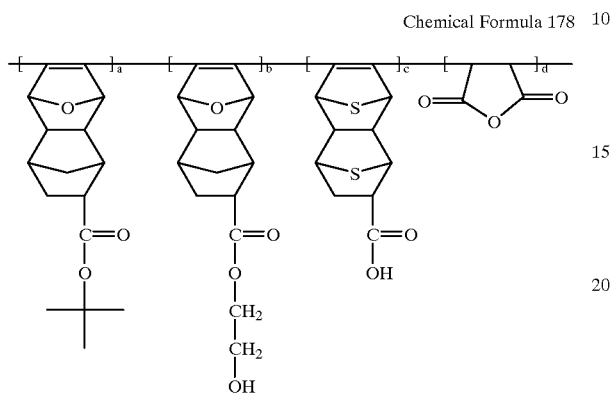

EXAMPLE 79

The procedure according to Example 76 is repeated but using 12-oxatetracyclo[4.4.0.1.1]dodec-7-ene-2,3-dicarboxylic acid monomer (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2,3-dicarboxylic acid/2-hydroxyethyl 12-oxatetracyclo[4.4.0.1.1]dodec-7-ene-2-carboxylate/maleic anhydride) represented by the following Chemical Formula 179:

Chemical Formula 179

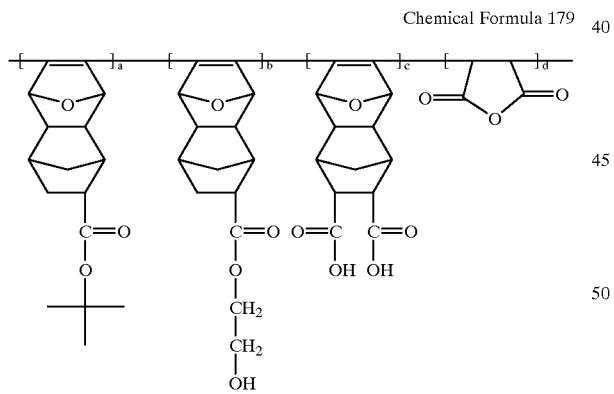

EXAMPLE 80

The procedure according to Example 76 is repeated but using 11,12-dioxatetracyclo[4.4.0.1.1]dodec-7-ene-2,3-dicarboxylic acid monomer (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/11,12-dioxatetracyclo[4.4.0.1.1]dodec-7-ene-2,3-dicarboxylic acid/2-hydroxyethyl 12-oxatetracyclo[4.4.0.1.1]dodec-7-ene-2-carboxylate/maleic anhydride) represented by the following Chemical Formula 180:

Chemical Formula 180

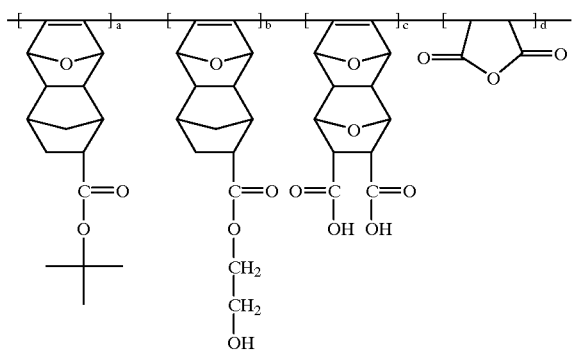

EXAMPLE 81

In tetrahydrofuran, dissolved are (i) tert-butyl 12-oxatetracyclo[4.4.0.1.1]dodec-7-ene-2-carboxylate (0.8 mole) as the first comonomer, (ii) 2-hydroxyethyl 11,12-dioxatetracyclo[4.4.0.1.1]dodec-7-ene-2-carboxylate (0.15 mole) as the second comonomer, (iii) 12-oxatetracyclo[4.4.0.1.1]dodec-7-ene-2-carboxylic acid (0.05 mole) as the third comonomer, and (iv) maleic anhydride (1.0 mole) as the polymerization-enhancing comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(1,1-dimethylethyl 12-oxatetracyclo[4.4.0.1.1] dodec-7-ene-2-carboxylate/12-oxatetracyclo[4.4.0.1.1]dodec-7-ene-2-carboxylic acid/2-hydroxyethyl 11,12-dioxatetracyclo[4.4.0.1.1]dodec-7-ene-2-carboxylate/maleic anhydride) represented by the following Chemical Formula 181:

Chemical Formula 181

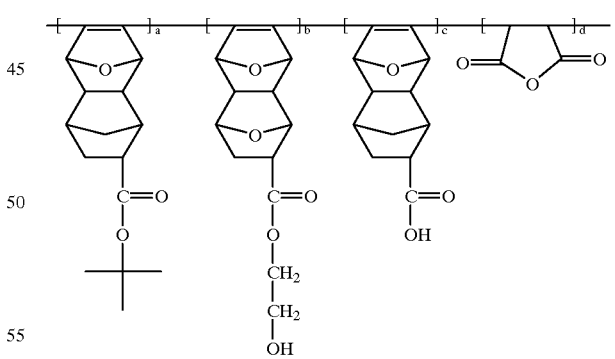

EXAMPLE 82

The procedure according to Example 81 is repeated but using 11,12-dioxatetracyclo[4.4.0.1.1]dodec-7-ene-2-carboxylic acid (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/11,12-dioxatetracyclo[4.4.0.1.1]dodec-7-ene-2-carboxylic acid/2-hydroxyethyl 11,12-dioxatetracyclo[4.4.0.1.1]dodec- 7-ene-2-carboxylate/maleic anhydride) represented by the following Chemical Formula 182:

Chemical Formula 182

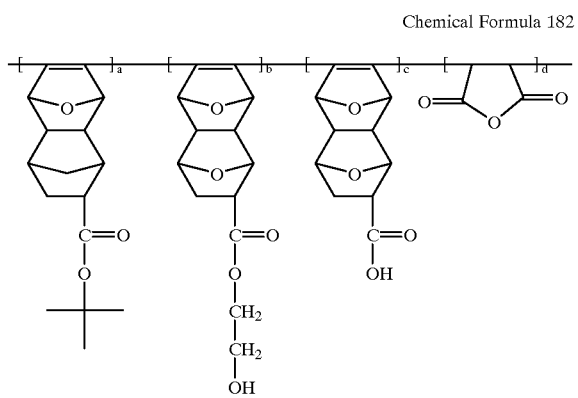

EXAMPLE 83

The procedure according to Example 81 is repeated but using 11,12-dithiatetracyclo[4.4.0.1.1]dodec-7-ene-2-carboxylic acid (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/11,12-dithiatetracyclo[4.4.0.1.1]dodec-7-ene-2-carboxylic acid/2-hydroxyethyl 11,12-dioxatetracyclo[4.4.0.1.1]dodec-7-ene-2-carboxylate/maleic anhydride) represented by the following Chemical Formula 183:

Chemical Formula 183

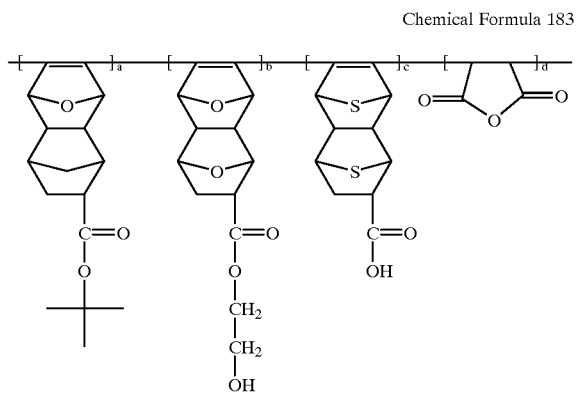

EXAMPLE 84

The procedure according to Example 81 is repeated but using 12-oxatetracyclo[4.4.0.1.1]dodec-7-ene-2-carboxylic acid (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2,3-dicarboxylic acid/ 2-hydroxyethyl 11,12-dioxatetracyclo[4.4.0.1.1]dodec-7-ene-2-carboxylate/maleic anhydride) represented by the following Chemical Formula 184:

Chemical Formula 184

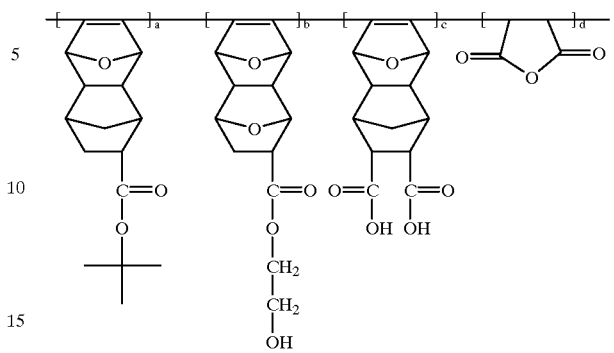

EXAMPLE 85

The procedure according to Example 81 is repeated but using 11,12-dioxatetracyclo[4.4.0.1.1]dodec-7-ene-2,3-dicarboxylic acid (0.05 mole) as the third comonomer instead of 12-oxatetracyclo[4.4.0.1.1]dodec-7-ene-2-carboxylic acid (0.05 mole), to obtain poly(1,1-dimethylethyl 12-oxatetracyclo[4.4.0.1.1]dodec-7-ene-2-carboxylate/11,12-dioxatetracyclo[4.4.0.1.1]dodec-7-ene-2,3-dicarboxylic acid/2-hydroxyethyl 11,12-dioxatetracyclo[4.4.0.1.1]dodec-7-ene-2-carboxylate/maleic anhydride) represented by the following Chemical Formula 185:

Chemical Formula 185

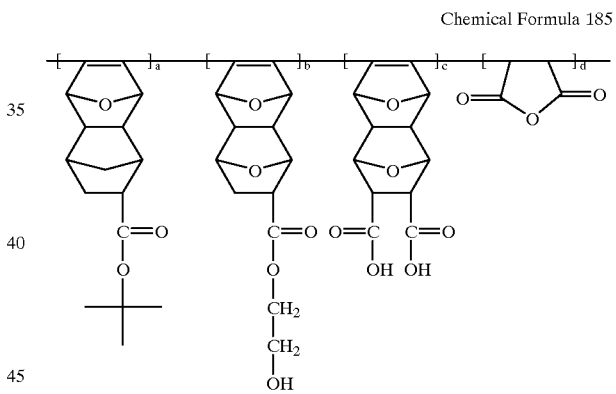

EXAMPLE 86

In tetrahydrofuran, dissolved are (i) tert-butyl 7-oxabicyclo[2.2.1]hept-5-ene-2-carboxylate (0.8 mole) as the first comonomer, (ii) 2-hydroxyethyl 12-oxatetracyclo [4.4.0.1.1]dodec-7-ene-2-carboxylate (0.13 mole) as the second comonomer, (iii) 15,16,17-trioxahexacyclo [6.6.1.1.1.0.0]heptadec-9-ene-2-carboxylic acid (0.07 mole) as the third comonomer, and (iv) maleic anhydride (1.0 mole) as the polymerization-enhancing comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(1,1-dimethylethyl 7-oxabicyclo[2.2.1]hept-5-ene-2-carboxylate/15,16,17-trioxahexacyclo[6.6.1.1.1.0.0]heptadec-9-ene-2-carboxylic acid/2-hydroxyethyl 12-oxatetracyclo[4.4.0.1.1]dodec-7- ene-2-carboxylate/maleic anhydride) represented by the following Chemical Formula 186:

Chemical Formula 186

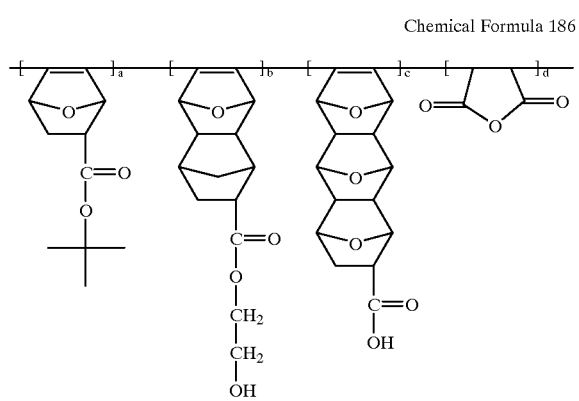

EXAMPLE 87

The procedure according to Example 86 is repeated but using 15,16,17-trioxahexacyclo[6.6.1.1.1.0.0]heptadec-9-ene-2,3-dicarboxylic acid monomer (0.07 mole) as the third comonomer instead of 15,16,17-trioxahexacyclo[6.6.1.1.1.0.0]heptadec-9-ene-2-carboxylic acid (0.07 mole), to obtain poly(1,1-dimethylethyl 7-oxabicyclo[2.2.1]hept-5-ene-2-carboxylate/15,16,17-trioxahexacyclo[6.6.1.1.1.0.0]heptadec-9-ene-2,3-dicarboxylic acid/2-hydroxyethyl 12-oxatetracyclo[4.4.0.1.1]dodec-7-ene-2-carboxylate/maleic anhydride) represented by the following Chemical Formula 187:

Chemical Formula 187

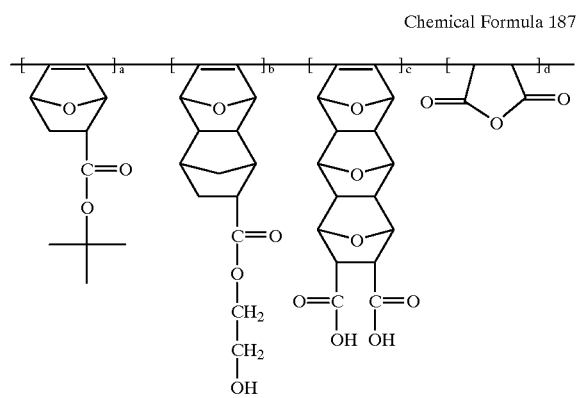

EXAMPLE 88

The procedure according to Example 86 is repeated but using 16,17-dioxahexacyclo[6.6.1.1.1.0.0]heptadec-9-ene-2,3-dicarboxylic acid monomer (0.07 mole) as the third comonomer instead of 15,16,17-trioxahexacyclo[6.6.1.1.1.0.0]heptadec-9-ene-2-carboxylic acid (0.07 mole), to obtain poly(1,1-dimethylethyl 7-oxabicyclo[2.2.1]hept-5-ene-2-carboxylate/16,17-dioxahexacyclo[6.6.1.1.1.0.0]heptadec-9-ene-2,3-dicarboxylic acid/2-hydroxyethyl 12-oxatetracyclo[4.4.0.1.1]dodec-7-ene-2-carboxylate/maleic anhydride) represented by the following Chemical Formula 188:

Chemical Formula 188

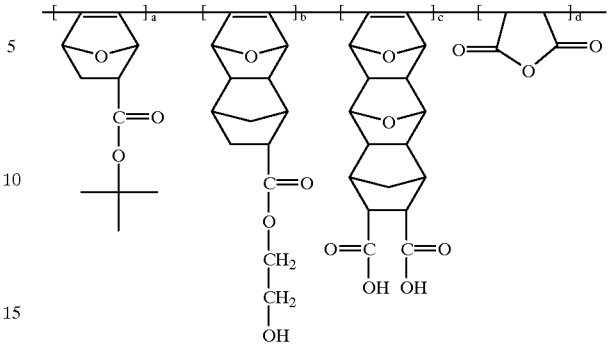

EXAMPLE 89

In tetrahydrofuran, dissolved are (i) tert-butyl 7-oxabicyclo[2.2.1]hept-5-ene-2-carboxylate monomer (0.90 mole) as the first comonomer, (ii) 16,17-dioxahexacyclo[6.6.1.1.1.0.0]heptadec-9-ene-2,2-dicarboxylic acid (0.10 mole) as the third comonomer, and (iii) maleic anhydride (1.0 mole) as the polymerization-enhancing comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(tert-butyl 7-oxabicyclo[2.2.1]hept-5-ene-2-carboxylate/15,16,17-trioxahexacyclo[6.6.1.1.1.0.0]heptadec-9-ene-2-carboxylic acid/maleic anhydride) represented by the following Chemical Formula 189:

Chemical Formula 189

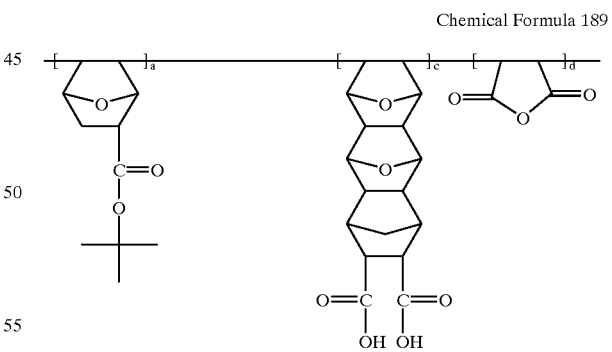

EXAMPLE 90

In tetrahydrofuran, dissolved are (i) 1,1-dimethylethyl 7-bicyclo[2.2.1]hept-5-ene-2-carboxylate (0.80 mole) as the first comonomer, (ii) 2-hydroxyethyl 12-oxatetracyclo[4.4.0.1.1]dodec-7-ene-2-carboxylate (0.20 mole) as the second comonomer, and (iii) maleic anhydride (1.0 mole) as the third comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(1,1-dimethylethyl 7-oxabicyclo[2.2.1]hept-5-ene-2-carboxylate/2-hydroxyethyl 12-oxatetracyclo[4.4.0.1.1]dodec-7-ene-2-carboxylate/maleic anhydride) represented by the following Chemical Formula 190:

Chemical Formula 190

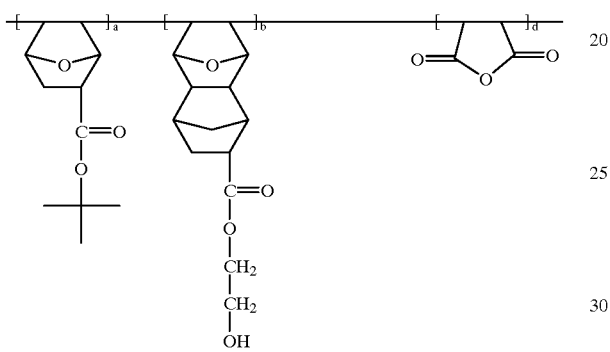

EXAMPLE 91

In tetrahydrofuran, dissolved are (i) tert-butyl 7-oxabicyclo[2.2.1]hept-5-ene-2-carboxylate (0.70 mole) as the first comonomer, (ii) 2-hydroxyethyl 12-oxatetracyclo[4.4.0.1.1]dodec-7-ene-2-carboxylate (0.10 mole) as the second comonomer, (iii) tert-butyl 12-oxatetracyclo[4.4.0.1.1]dodec-7-ene-2,3-dicarboxylic acid (0.2 mole) as the third comonomer, and (iv) maleic anhydride (1.0 mole) as the polymerization-enhancing comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(tert-butyl 12-oxatetracyclo [4.4.0.1.1]dodec-7-ene-2,3-dicarboxylic acid/tert-butyl 7-oxabicyclo[2.2.1]hept-5-ene-2-carboxylate/2-hydroxyethyl 12-oxatetracyclo[4.4.0.1.1]dodec-7-ene-2-carboxylate/maleic anhydride) represented by the following Chemical Formula 191:

Chemical Formula 191

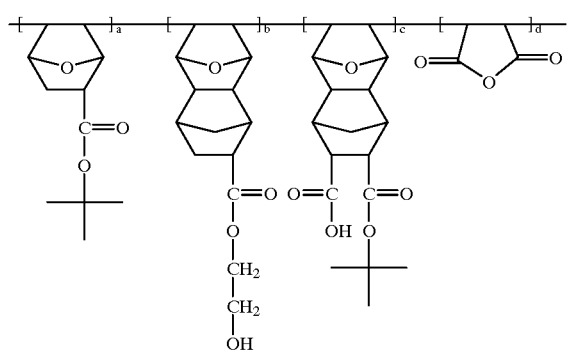

EXAMPLE 92

In tetrahydrofuran, dissolved are (i) tert-butyl 12-oxatetracyclo[4.4.0.1.1]dodec-7-ene-2-carboxylate (0.83 mole) as the first comonomer, (ii) 2-hydroxyethyl 12-oxatetracyclo[4.4.0.1.1]dodec-7-ene-2-carboxylate (0.10 mole) as the second comonomer, (iii) 2-methyl 12-oxatetracyclo[4.4.0.1.1]dodec-7-ene-2-carboxylic acid (0.07 mole) as the third comonomer, and (iv) maleic anhydride (1.0 mole) as the polymerization-enhancing comonomer. Then, AIBN (azobisisobutyronitrile) is added thereto as a polymerization initiator in an amount of 2 wt % based on total weight of the monomers employed. The resultant mixture is reacted at a temperature between about 60 and 700° C. for 4 to 24 hours under nitrogen or argon atmosphere.

The resultant material is precipitated from ethyl ether or hexane and dried to obtain poly(tert-butyl 12-oxatetracyclo [4.4.0.1.1]dodec-7-ene-2-carboxylate/2-methyl 12-oxatetracyclo[4.4.0.1.1]dodec-7-ene-2-carboxylic acid/ 2-hydroxyethyl 12-oxatetracyclo[4.4.0.1.1]dodec-7-ene-2-carboxylate/maleic anhydride) represented by the following Chemical Formula 192:

Chemical Formula 192

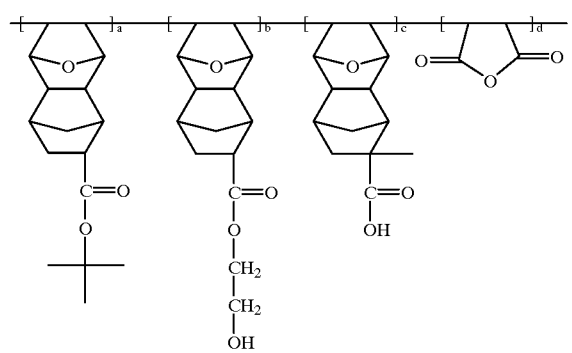

EXAMPLE 93

The procedure according to Example 92 is repeated but using 2-methyl-11,12-dioxatetracyclo[4.4.0.1.1]dodec-7-ene-2-carboxylic acid (0.07 mole) as the third comonomer instead of 2-methyl-12-oxatetracyclo[4.4.0.1.1]dodec-7-ene-2-carboxylic acid monomer (0.07 mole), to obtain poly (tert-butyl 12-oxatetracyclo[4.4.0.1.1]dodec-7-ene-2-carboxylate/2-methyl-11,12-dioxatetracyclo[4.4.0.1.1]dodec-7-ene-2-carboxylic acid/2-hydroxyethyl 12-oxatetracyclo[4.4.0.1.1]dodec-7-ene-2-carboxylate/maleic anhydride) represented by the following Chemical Formula 193:

Chemical Formula 193

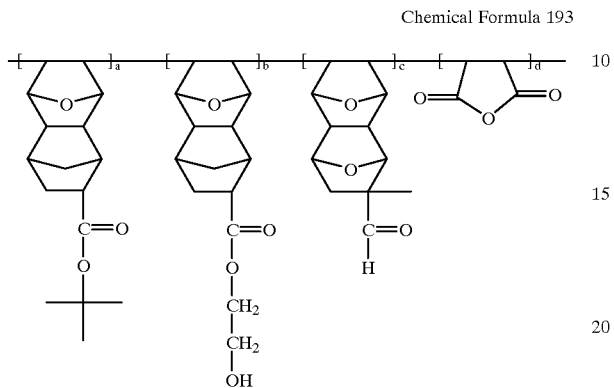

EXAMPLE 94

The procedure according to Example 76 is repeated but using tert-butyl 2-methyl-12-oxatetracyclo[4.4.0.1.1]dodec-7-ene-2-carboxylate (0.07 mole) as the first comonomer instead of tert-butyl 12-oxatetracyclo[4.4.0.1.1]dodec-7-ene-2-carboxylate (0.07 mole), to obtain poly(tert-butyl 2-methyl-12-oxatetracyclo[4.4.0.1.1]dodec-7-ene-2-carboxylate/12-oxatetracyclo[4.4.0.1.1]dodec-7-ene-2-carboxylic acid/2-hydroxyethyl 12-oxatetracyclo[4.4.0.1.1]dodec-7-ene-2-carboxylate/maleic anhydride) represented by the following Chemical Formula 194:

Chemical Formula 194

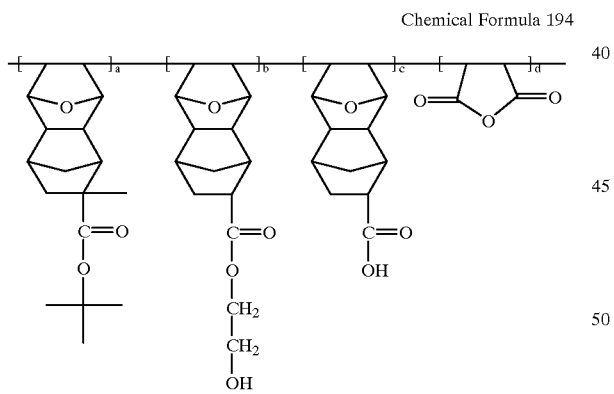

EXAMPLE 95

The procedure according to Example 76 is repeated but using 3-hydroxypropyl 12-oxatetracyclo[4.4.0.1.1]dodec-7-ene-2-carboxylate (0.15 mole) as the second comonomer instead of 2-hydroxyethyl 12-oxatetracyclo[4.4.0.1.1]dodec-7-ene-2-carboxylate (0.15 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/3-hydroxypropyl 12-oxatetracyclo[4.4.0.1.1]dodec-7-ene-2-carboxylate/maleic anhydride) represented by the following Chemical Formula 195:

Chemical Formula 195

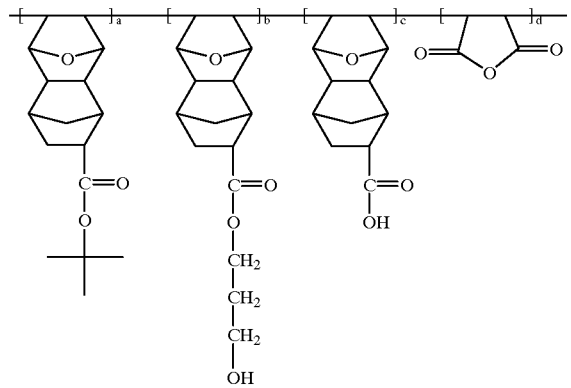

EXAMPLE 96

The procedure according to Example 76 is repeated but using 3-hydroxypropyl 12-oxatetracyclo[4.4.0.1.1]dodec-7-ene-2-carboxylate as the second comonomer instead of 2-hydroxyethyl 12-oxatetracyclo[4.4.0.1.1]dodec-7-ene-2-carboxylate (0.15 mole), and methyl 12-oxatetracyclo[4.4.0.1.1]dodecne-2,3-dicarboxylic acid (0.15 mole) as the third comonomer instead of 12-oxatetracyclo[4.4.0.1.1]dodec-7-ene-2-carboxylic acid monomer, to obtain poly(1,1-dimethylethyl 12-oxatetracyclo[4.4.0.1.1]dodec-7-ene-2-carboxylate/methyl 12-oxatetracyclo[4.4.0.1.1]dodec-7-ene-2,3-dicarboxylic acid/3-hydroxypropyl 12-oxatetracyclo[4.4.0.1.1]dodec-7-ene-2-carboxylate/maleic anhydride) represented by the following Chemical Formula 196:

Chemical Formula 196

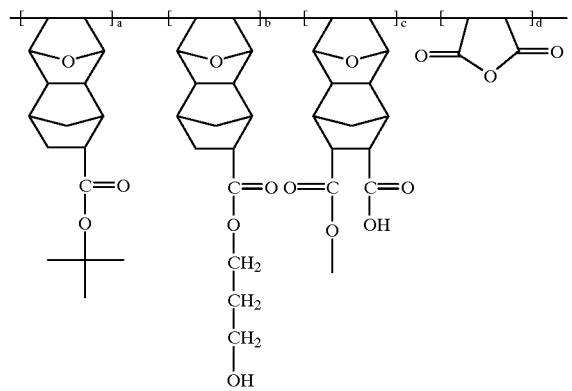

EXAMPLE 97

The procedure according to Example 76 is repeated but using 2-hydroxyethyl 11,12-dithiatetracyclo[4.4.0.1.1]dodec-7-ene-2-carboxylate (0.15 mole) as the second comonomer instead of 2-hydroxyethyl 12-oxatetracyclo[4.4.0.1.1]dodec-7-ene-2-carboxylate, to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/11,12-dithiatetracyclo[4.4.0.1.1]dodec-7-ene-2-carboxylate/maleic anhydride) represented by the following Chemical Formula 197:

Chemical Formula 197

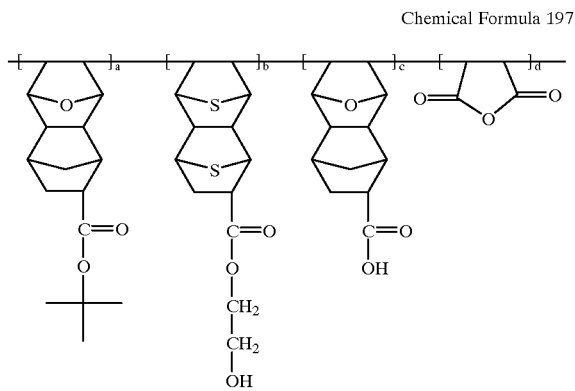

In Examples 76 to 97, maleic anhydride (1.0 mole) is used as the polymerization-enhancing comonomer, however, N-methyl maleimide or N-ethyl maleimide (1.0 mole) may be used instead. The following Examples disclose the copolymers comprising a maleimide derivative as the polymerization-enhancing comonomer.

EXAMPLE 98

The procedure according to Example 76 is repeated but using N-methyl maleimide (1.0 mole) as the polymerization-enhancing comonomer instead of maleic anhydride (1.0 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/2-hydroxyethyl 12-oxatetracyclo[4.4.0.1.1]dodec-7-ene-2-carboxylate/N-methyl maleimide) represented by the following Chemical Formula 198:

Chemical Formula 198

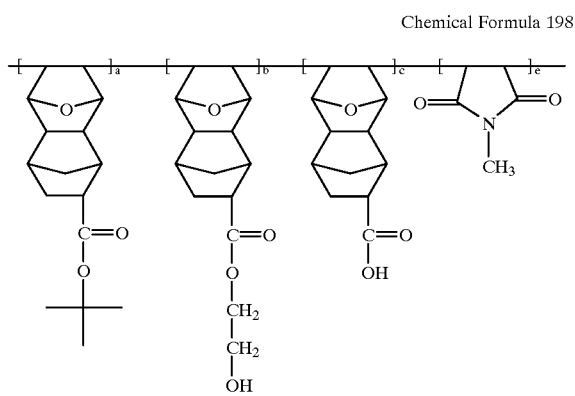

EXAMPLE 99

The procedure according to Example 76 is repeated but using N-ethyl maleimide (1.0 mole) as the polymerization-enhancing comonomer instead of maleic anhydride (1.0 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/2-hydroxyethyl 12-oxatetracyclo[4.4.0.1.1]dodec-7-ene-2-carboxylate/N-ethyl maleimide) represented by the following Chemical Formula 199:

Chemical Formula 199

EXAMPLE 100

The procedure according to Example 76 is repeated but using N-ethyl maleimide (0.5 mole) and maleic anhydride (0.5 mole) as the polymerization-enhancing comonomer instead of maleic anhydride (1.0 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/2-hydroxyethyl 12-oxatetracyclo[4.4.0.1.1]dodec-7-ene-2-carboxylate/N-ethyl maleimide/maleic anhydride) represented by the following Chemical Formula 400:

Chemical Formula 400

EXAMPLE 101

The procedure according to Example 76 is repeated but using N-methyl maleimide (0.5 mole) and maleic anhydride (0.5 mole) as the polymerization-enhancing comonomer instead of maleic anhydride (1.0 mole), to obtain poly(1,1-dimethylethyl 12-oxatetracyclo[4.4.0.1.1]dodec-7-ene-2-carboxylate/12-oxatetracyclo[4.4.0.1.1]dodec-7-ene-2-carboxylic acid/2-hydroxyethyl 12-oxatetracyclo[4.4.0.1.1]dodec-7-ene-2-carboxylate/N-methyl maleimide/maleic anhydride) represented by the following Chemical Formula 401:

Chemical Formula 401

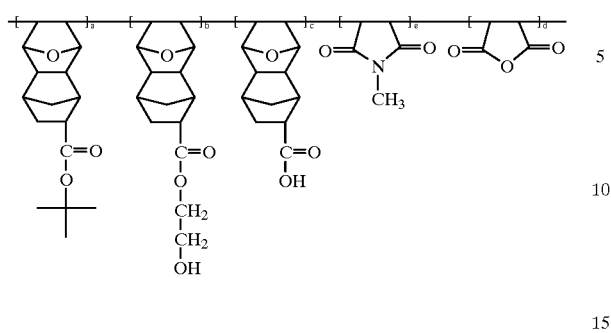

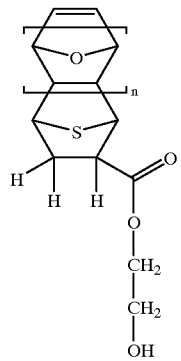

Chemical Formula 103

EXAMPLE 102

The photoresist copolymer obtained from Example 76 (10 g) is dissolved in 60 g of propylene glycol methyl ether acetate solvent, and triphenylsulfonium triflate or dibutyl naphthyl sulfonium triflate (0.12 g) as a photoacid generator is added thereto. After stirring, the resultant mixture is filtered through a 0.10 □m filter to prepare a photoresist composition.

The photoresist composition (1 ml) thus obtained is spin-coated on a silicon wafer, baked at 1100° C. for 90 seconds and exposed to light by using ArF laser exposer. After baking, the photoresist is developed in 2.38 wt % aqueous tetramethylammonium hydroxide (TMAH) solution for 40 seconds. Then it is baked again at 1100° C. for 90 seconds to obtain an L/S pattern of 0.11 $\mu$m.

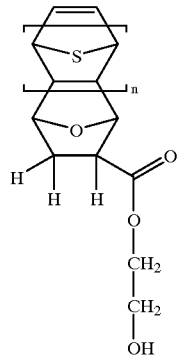

Chemical Formula 104

What is claimed is:

1. A photoresist monomer represented by the following Chemical Formula 1:

Chemical Formula 1

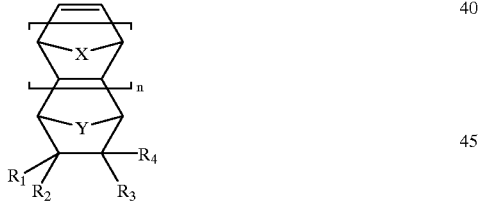

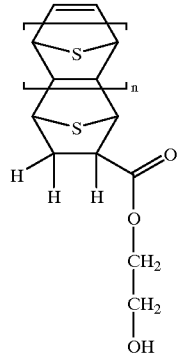

Chemical Formula 105 wherein, X and Y individually represent oxygen, sulfur, $CH_2$ or $C_2CH_2$; n represents an integer of 1 to 5; and $R_1$, $R_2$, $R_3$ and $R_4$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain; provided that at least one of $R_1$ to $R_4$ represent(s) —COO—R'—OH wherein R' is an alkyl group with or without substituent(s) on its linear or branched chain.

2. A photoresist monomer according to claim 1, which is selected from the group consisting of the compounds represented by one of the following Chemical Formulas 103 to 108 and 111 to 116:

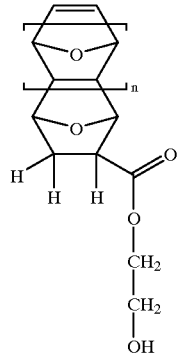

Chemical Formula 106

-continued
Chemical Formula 107
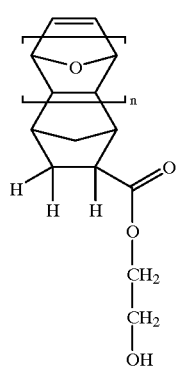
Chemical Formula 108
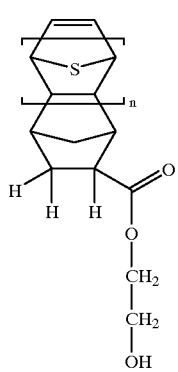
Chemical Formula 111
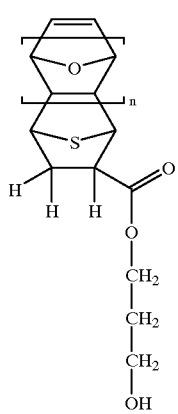
-continued
Chemical Formula 112
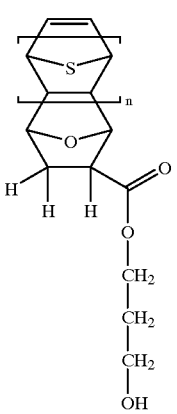
Chemical Formula 113
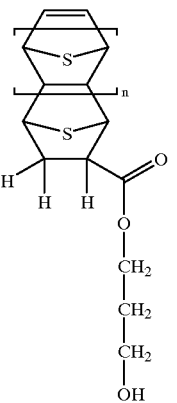
Chemical Formula 114
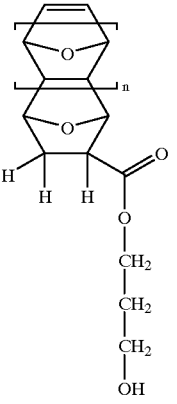
Chemical Formula 115
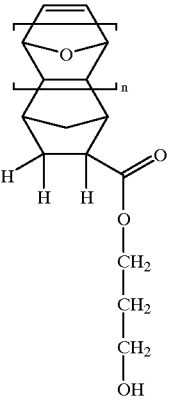

-continued

Chemical Formula 116

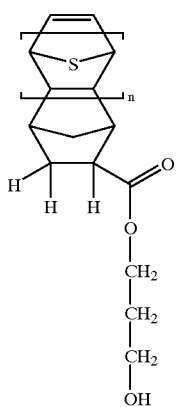

wherein, n is an integer of 1 to 5.

3. A process for preparing a photoresist monomer, which comprises the steps of (a) performing Diels-Alder reaction of a compound of Chemical Formula 2:

Chemical Formula 2

wherein Y is oxygen, sulfur, $CH_2$ or $CH_2CH_2$ with a compound of Chemical Formula 3:

Chemical Formula 3

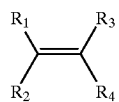

wherein $R_1$, $R_2$, $R_3$ and $R_4$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain; provided that at least one of $R_1$ to $R_4$ represent(s) —COO—R'—OH wherein R' is an alkyl group with or without substituent(s) on its linear or branched chain; to give a compound of Chemical Formula 2x:

Chemical Formula 2x

Chemical Formula 2x

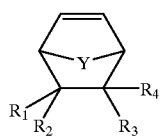

and (b) performing another Diels-Alder reaction of the obtained compound of Chemical Formula 2x above with a compound of Chemical Formula 4:

Chemical Formula 4

wherein X is oxygen, sulfur, $CH_2$ or $CH_2CH_2$ to obtain a compound of Chemical Formula 1:

Chemical Formula 1

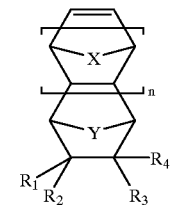

wherein n is an integer from 1 to 5.

4. A photoresist copolymer which comprises at least one repeating unit derived from the monomer represented by the following Chemical Formula 1:

Chemical Formula 1

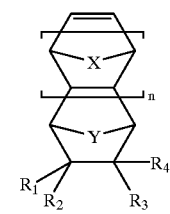

wherein, X and Y individually represent oxygen, sulfur, $CH_2$ or $CH_2CH_2$; n represents an integer of 1 to 5; and $R_1$, $R_2$, $R_3$ and $R_4$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain; provided that at least one of $R_1$ to $R_4$ represent(s) —COO—R'—OH wherein R' is an alkyl group with or without substituent(s) on its linear or branched chain.

5. A photoresist copolymer according to claim 4 further comprising repeating units derived from a second monomer represented by the following Chemical Formula 5:

Chemical Formula 5

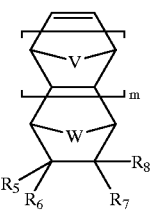

wherein V and W individually represent oxygen, sulfur, $CH_2$ or $CH_2CH_2$; m is an integer of 0 to 5; and $R_5$ to $R_8$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain; provided that at least one of $R_5$ to $R_8$ represent(s) —R"—COO—R wherein R" is a linear or branched alkyl group, and R is an acid labile protective group.

6. A photoresist copolymer according to claim 5 wherein the compound of Chemical Formula 5 is selected from the group consisting of the compounds represented by one of Chemical Formulas 117 to 141:

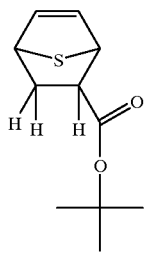

Chemical Formula 117

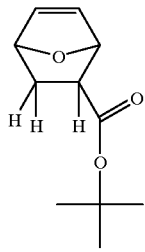

Chemical Formula 118

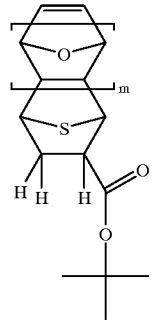

Chemical Formula 119

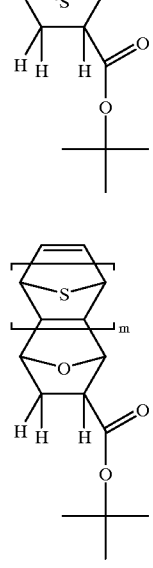

Chemical Formula 120

-continued

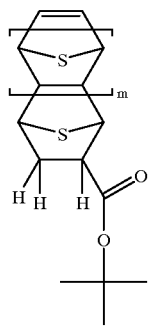

Chemical Formula 121

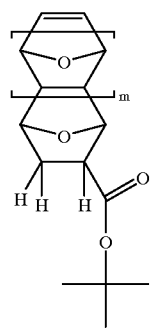

Chemical Formula 122

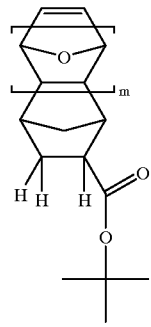

Chemical Formula 123

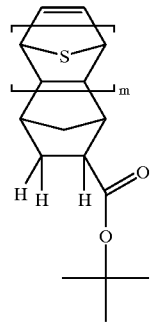

Chemical Formula 124

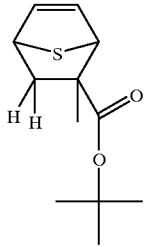

Chemical Formula 125

Chemical Formula 126
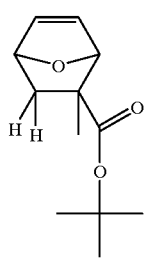
Chemical Formula 127
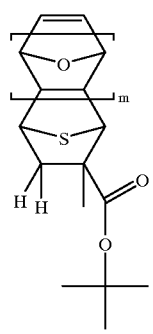
Chemical Formula 128
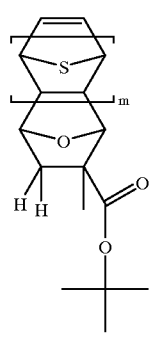
Chemical Formula 129
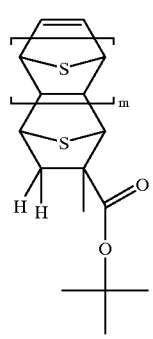
Chemical Formula 130
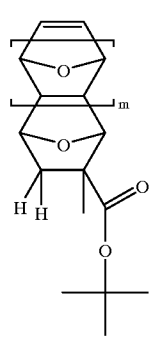
Chemical Formula 131
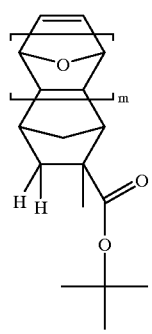
Chemical Formula 132
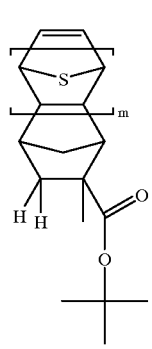
Chemical Formula 133
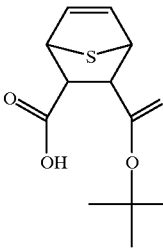
Chemical Formula 134
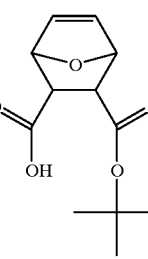
Chemical Formula 135
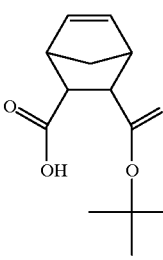

Chemical Formula 136

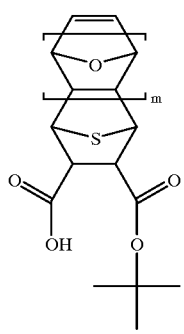

Chemical Formula 137

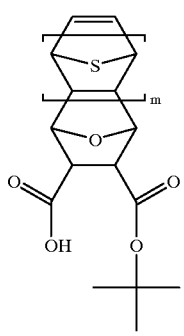

Chemical Formula 138

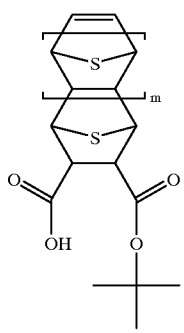

Chemical Formula 139

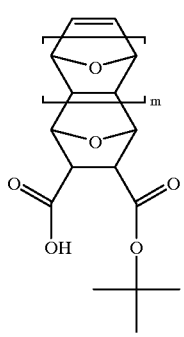

Chemical Formula 140

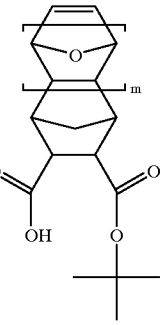

Chemical Formula 141

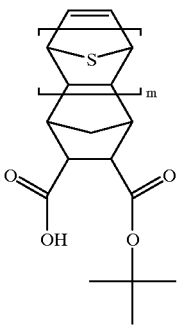

wherein m is an integer of 0 to 5.

7. A photoresist copolymer according to claim 5, which further comprises maleic anhydride and/or a maleimide derivative of Chemical Formula 8:

Chemical Formula 8

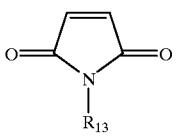

wherein $R_{13}$ is a linear or branched alkyl group.

8. A photoresist copolymer according to claim 7, wherein the maleimide derivative is N-methyl maleimide or N-ethyl maleimide.

9. A photoresist copolymer according to claim 5, which further comprises a monomer of the following Chemical Formula 6:

Chemical Formula 6

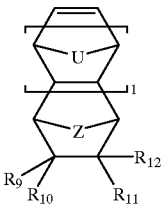

wherein, U and Z individually represent oxygen, sulfur, CH$_2$ or CH$_2$CH$_2$; 1 is an integer of 0 to 5; and R$_9$ to R$_{12}$ individually represent hydrogen, C$_1$–C$_{10}$ alkyl having substituent(s) on its main or branched chain, C$_1$–C$_{10}$ ester having substituent(s) on its main or branched chain, C$_1$–$_{10}$ ketone having substituent(s) on its main or branched chain, C$_1$–C$_{10}$ carboxylic acid having substituent(s) on its main or branched chain, C$_1$–C$_{10}$ acetal having substituent(s) on its main or branched chain; provided that at least one of R$_9$ to R$_{12}$ represent(s) —R'''—COOH wherein R''' is a linear or branched alkyl group.

10. A photoresist copolymer according to claim 9, wherein the compound of Chemical Formula 6 is selected from the group consisting of the compounds represented by one of the following Chemical Formulas 142 to 175

Chemical Formula 142

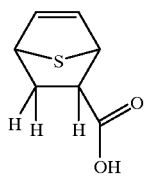

Chemical Formula 143

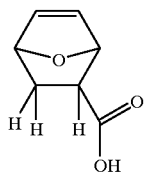

Chemical Formula 144

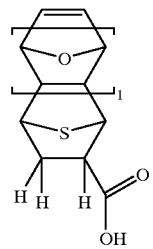

Chemical Formula 145

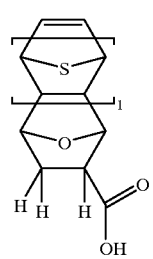

Chemical Formula 146

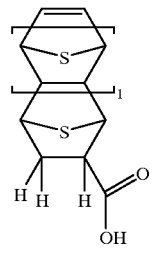

-continued

Chemical Formula 147

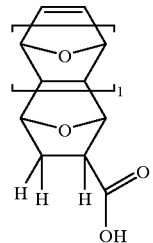

Chemical Formula 148

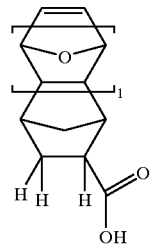

Chemical Formula 149

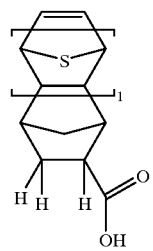

Chemical Formula 150

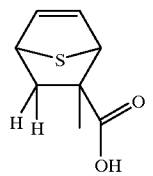

Chemical Formula 151

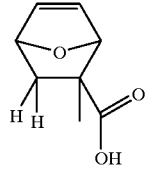

Chemical formula 152

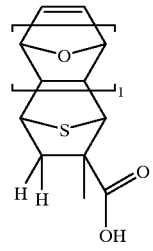

Chemical Formula 153
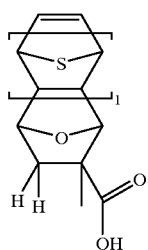
Chemical Formula 154
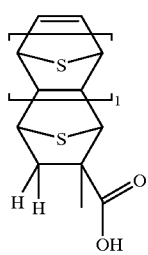
Chemical Formula 155
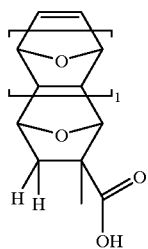
Chemical Formula 156
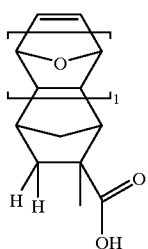
Chemical Formula 157
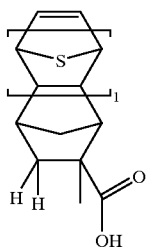
Chemical Formula 158
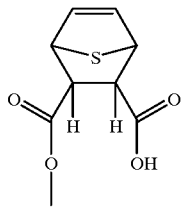
Chemical Formula 159
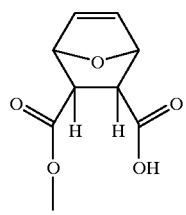
Chemical Formula 160
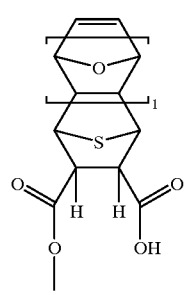
Chemical Formula 161
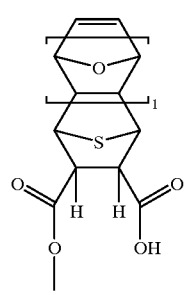
Chemical Formula 162
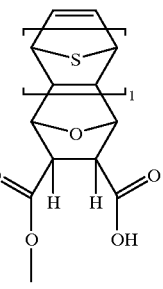
Chemical Formula 163
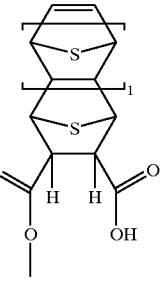

-continued
Chemical Formula 164
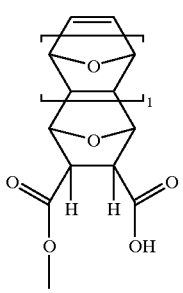
Chemical Formula 165
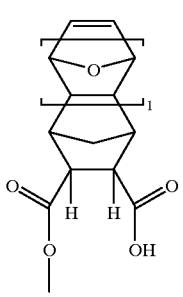
Chemical Formula 166
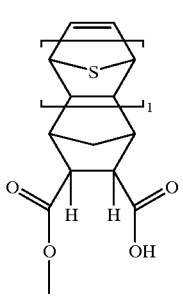
Chemical Formula 167
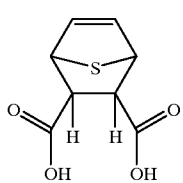
Chemical Formula 168
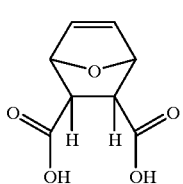
Chemical Formula 169
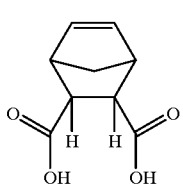
-continued
Chemical Formula 170
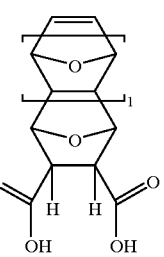
Chemical Formula 171
Chemical Formula 172
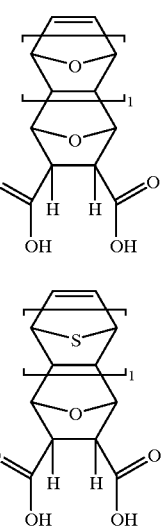
Chemical Formula 173
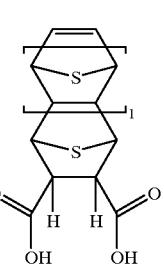
Chemical Formula 174
Chemical Formula 175
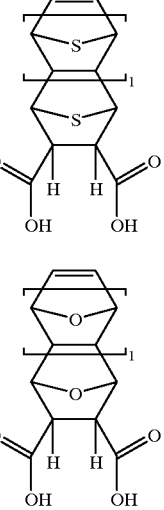
11. A photoresist copolymer according to claim 4 represented by the following Chemical Formula 300:

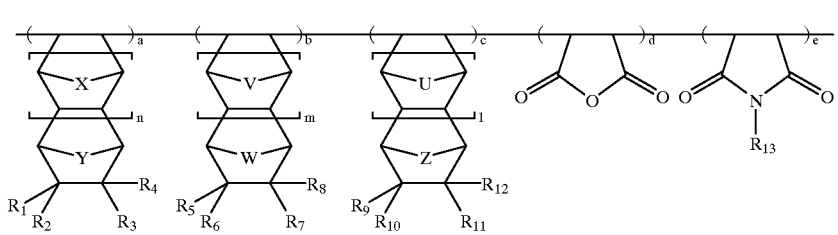

Chemical Formula 300 wherein, X, Y, V, W, U and Z individually represent oxygen, sulfur, $CH_2$ or $CH_2CH_2$; n represent an integer of 1 to 5, m and l individual represent an integer of 0 to 5; $R_1$ to $R_{12}$ represent hydrogen, $C_1-C_{10}$ alkyl having substituent(s) on its main or branched chain, $C_1-C_{10}$ ester having substituent(s) on its main or branched chain, $C_1-C_{10}$ ketone having substituent(s) on its main or branched chain, $C_1-C_{10}$ carboxylic acid having substituent(s) on its main or branched chain, $C_1-C_{10}$ acetal having substituent(s) on its main or branched chain; a, b, c, d and e individually represent polymerization ratio of each comonomer which is present, with the repeating units represented by a and b and/or c always being present and the units represented by d and/or e being optional; and $R_{13}$ is a linear or branched alkyl group; provided that at least one of $R_1$ to $R_4$ represent(s) —COO—R'—OH wherein R' is an alkyl group with or without substituent(s) on its linear or branched chain, at least one of $R_5$ to $R_8$ represent(s) —R"—COO—R wherein R" is a linear or branched alkyl group and R is an acid labile protective group, and at least one of $R_9$ to $R_{12}$ represent(s) —R'"—COOH wherein R'" is a linear or branched alkyl group.

12. A photoresist copolymer according to claim 11, which is selected from the group consisting of the compounds represented by one of Chemical Formulas 176 to 199, and 400 to 401:

Chemical Formula 176

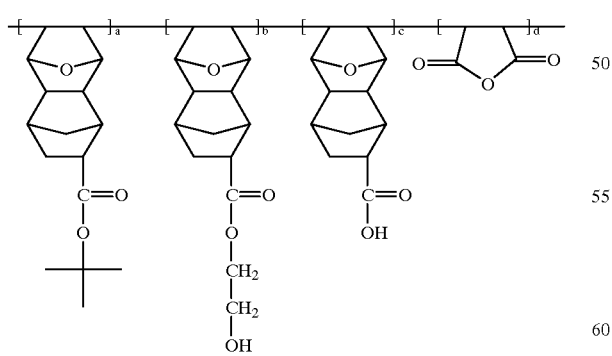

-continued

Chemical Formula 177

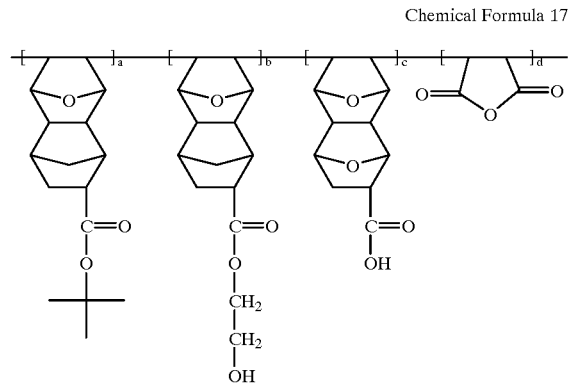

Chemical Formula 178

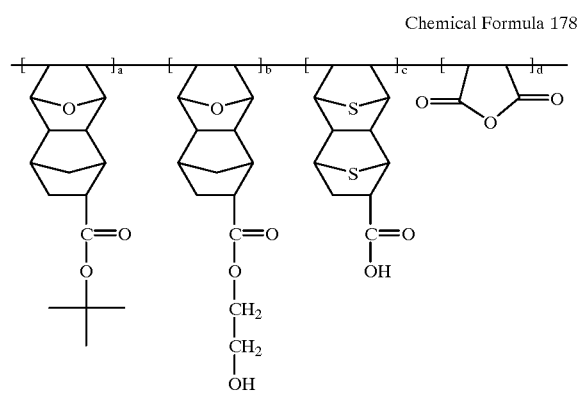

Chemical Formula 179

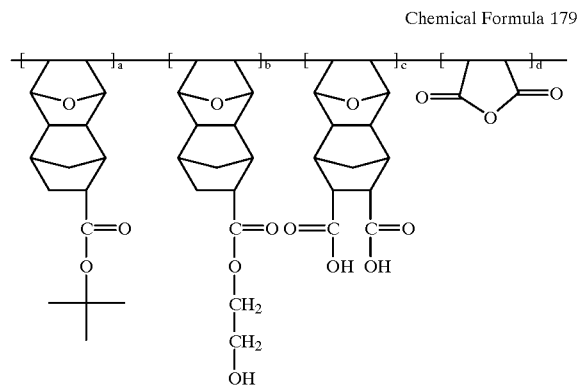

-continued
Chemical Formula 180
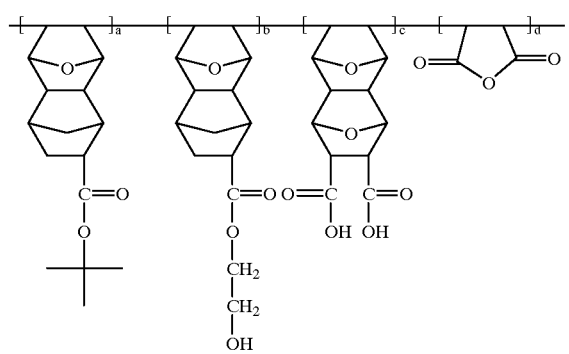
Chemical Formula 184
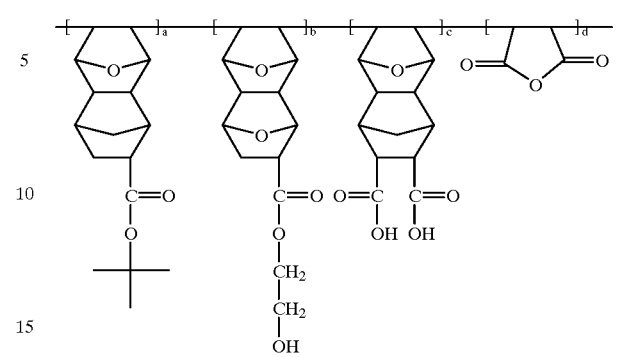
Chemical Formula 181
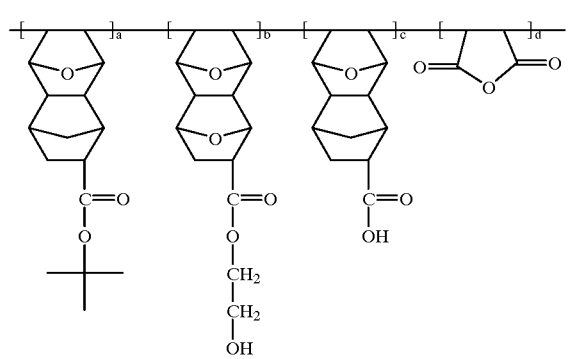
Chemical Formula 185
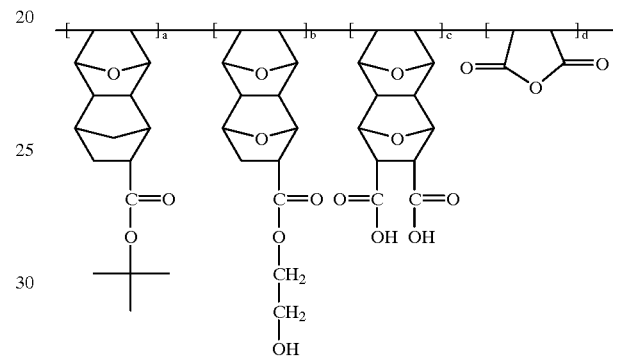
Chemical Formula 182
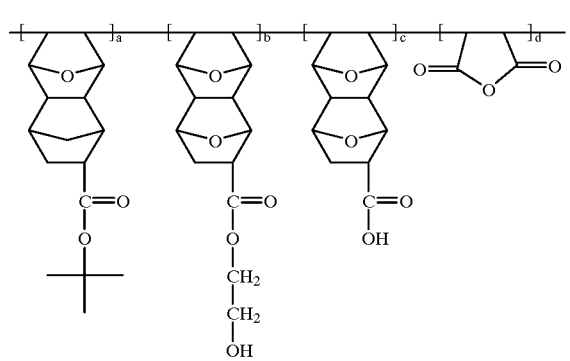
Chemical Formula 186
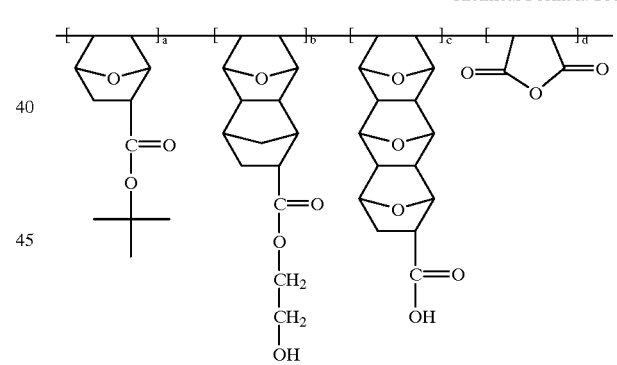
Chemical Formula 183
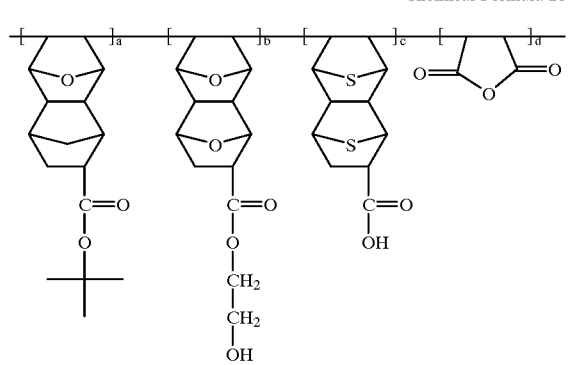
Chemical Formula 187
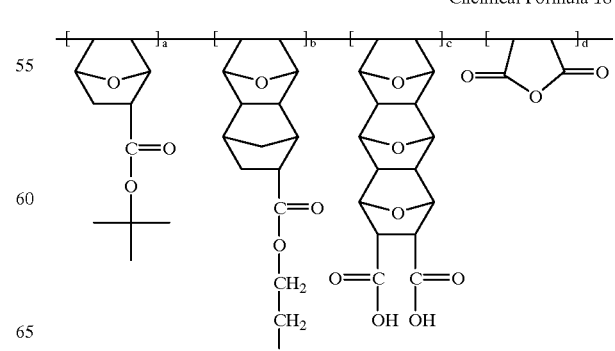

Chemical Formula 188
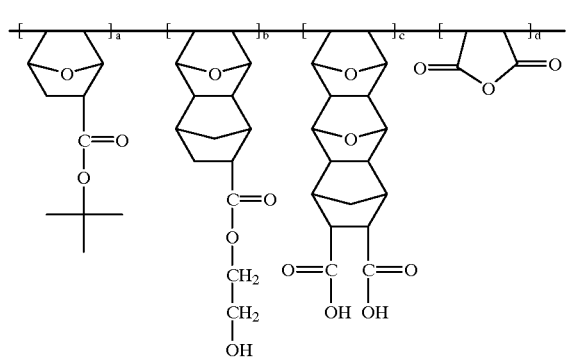
Chemical Formula 192
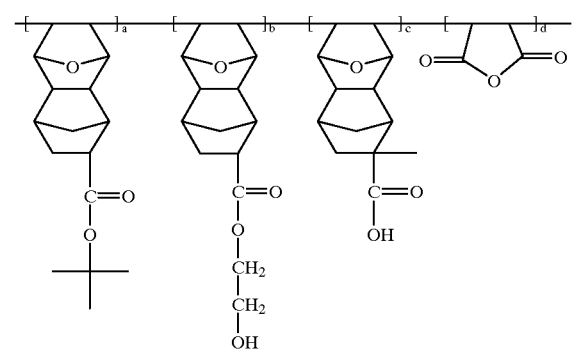
Chemical Formula 189
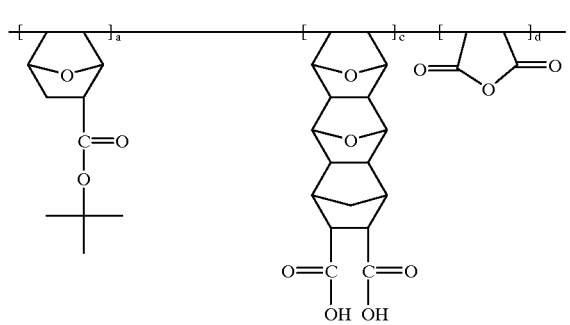
Chemical Formula 193
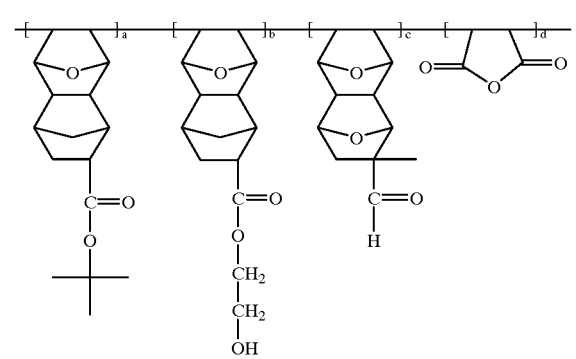
Chemical Formula 190
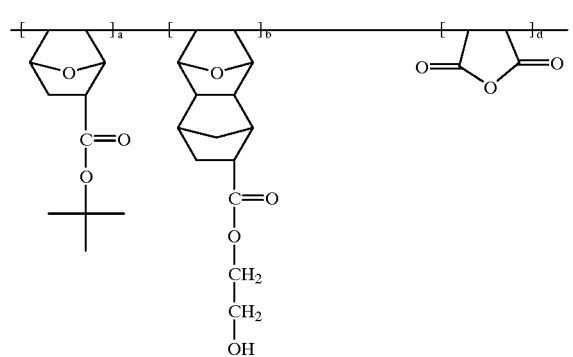
Chemical Formula 194
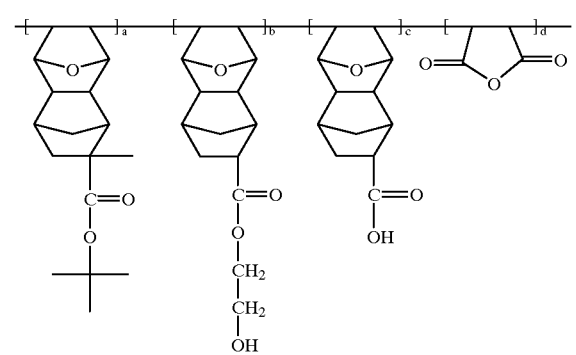
Chemical Formula 191
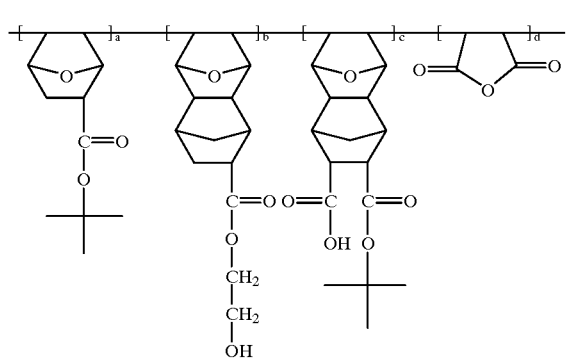
Chemical Formula 195
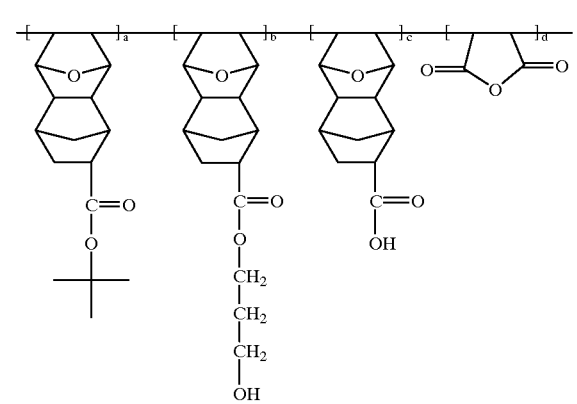

Chemical Formula 196

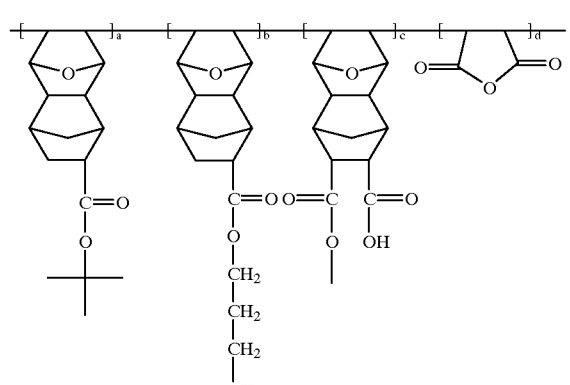

Chemical Formula 197

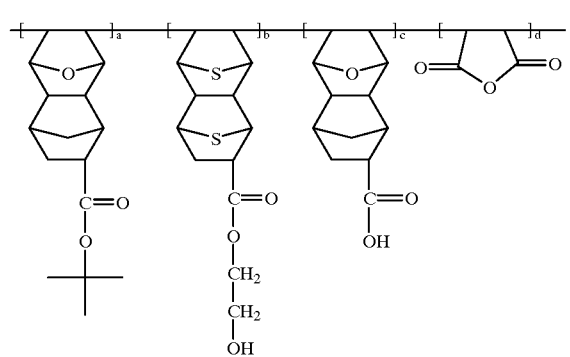

Chemical Formula 198

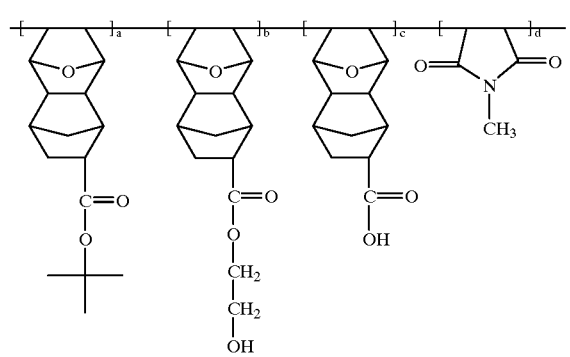

Chemical Formula 199

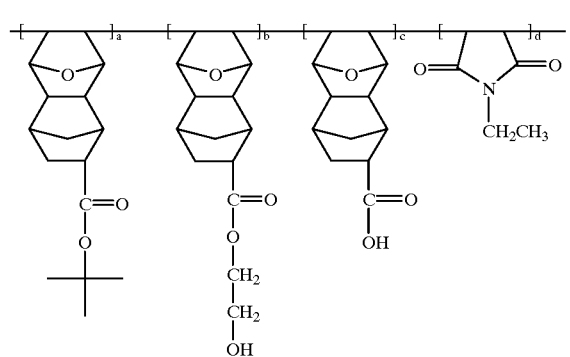

Chemical Formula 400

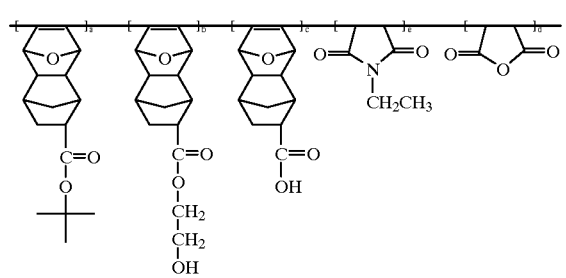

Chemical Formula 401

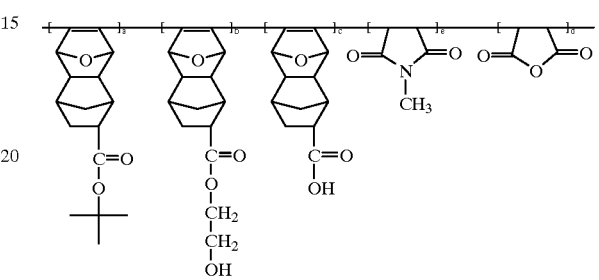

13. A process for preparing a photoresist copolymer, which comprises the steps of (a) dissolving a compound of Chemical Formula 1:

Chemical Formula 1

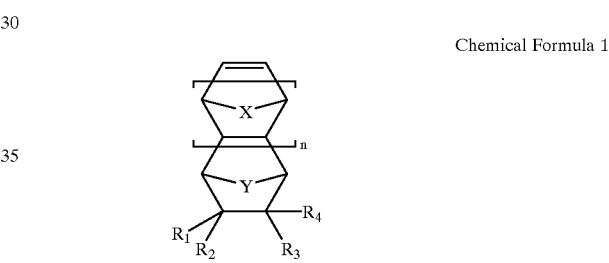

and at least one compound represented by the following Chemical Formulas 5 to 8 in organic solvent;

Chemical Formula 5

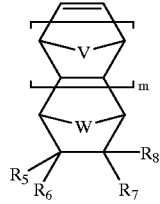

Chemical Formula 6

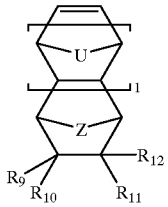

-continued

Chemical Formula 7

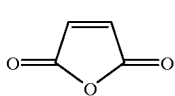

Chemical Formula 8

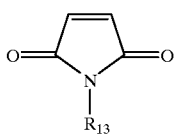

wherein X, Y, V, W, U and Z individually represent oxygen, sulfur $Ch_2$ or $CH_2CH_2$; represent from 1 to 5, m and 1 individually represent of 0 to 5; $R_1$ to $R_{12}$ individually represent hydrogen, $C_1$–$C_{10}$ alkyl substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its branched chain, $C_1$–$C_{10}$ acetal having substituent(s) on its main or branched chain; a, b, c, d and e individually represent polymerization ratio of each comonomer which is present; and $R_{13}$ is a linear or branched alkyl group; provided that at least one of $R_1$ to $R_4$ represent(s) —COO—R'—OH wherein R' is an alkyl group with or without substituent(s) on its linear or branched chain, at least one of $R_5$ to $R_8$ represent(s) —R"—COO—R wherein R" is a linear or branched alkyl group and R is an acid labile protective group, and at least one of $R_9$ to $R_{12}$ represent(s) —R'"—COOH wherein R'" is a linear or branched alkyl group;

and (b) adding a polymerization initiator thereto.

14. A process according to claim 13, wherein the organic solvent used in step (a) comprises one or more solvent(s) selected from the group consisting of cyclohexanone, methyl ethyl ketone, benzene, toluene, dioxane, tetrahydrofuran and dimethylformamide.

15. A process according to claim 13, wherein the polymerization initiator is a radical polymerization initiator.

16. A process according to claim 13, wherein the polymerization initiator is selected from the group consisting of benzoyl peroxide, 2,2'-azobisisobutyronitile (AIBN), acetyl peroxide, lauryl peroxide, tert-butyl peracetate, tert-butyl hydroperoxide and di-tert-butyl peroxide.

17. A process according to claim 13, wherein the polymerization initiator is used in an amount of 0.5 to 10 wt %, based on total weight of the reactants added in step (a).

18. A process according to claim 13, wherein the polymerization is performed at a temperature of 60 to 70° C. for 4 to 24 hours.

19. A photoresist composition comprising (i) a photoresist copolymer comprising a photoresist copolymer of claim 11, (ii) a photoacid generator, and (iii) organic solvent.

20. A photoresist composition according to claim 19 wherein the photoresist copolymer is used in an amount of 1 to 30% by weight of the organic solvent.

21. A photoresist composition according to claim 19 wherein the photoacid generator is used in an amount of 0.1 to 10% by weight of the photoresist copolymer.

22. A photoresist composition according to claim 19, wherein the organic solvent for polymerization comprises one or more compound(s) selected from the group consisting of methyl 3-methoxypropionate, ethyl 3-ethoxypropionate, propylene glycol methyl ether acetate and cyclohexanone.

23. A photoresist composition according to claim 19, wherein the photoacid generator is a sulfide or onium type.

24. A photoresist composition according to claim 19, wherein the photoacid generator is one or more compound (s) selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate.

25. A process for forming a photoresist pattern, which comprises the steps of (a) coating a photoresist composition of claim 19 on a wafer; (b) exposing the wafer to light; and (c) developing the resultant material with a developing solution to obtain a predetermined pattern.

26. A process according to claim 25, which further comprises a soft-baking step before step (b).

27. A process according to claim 25, which further comprises a post-baking step after step (c).

28. A process according to claim 26 or 27, wherein the baking step is performed at a temperature of 70 to 200° C.

29. A process according to claim 25, wherein the light exposure is carried out by using ArF, KrF, E-beam, X-ray, EUV, DUV or ion beam.

30. A process according to claim 25, wherein the light exposure is carried out by irradiating 1 to 100 mJ/cm2 of light-exposure energy.

31. A semiconductor element comprising a photoresist composition of claim 19 coated on a silicon wafer.

32. A method for synthesizing a photoresist copolymer, which comprises:

(a) dissolving a compound of Chemical Formula 1:

Chemical Formula 1

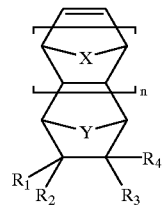

and at least one compound represented by the following Chemical Formulas 5 and 6 in organic solvent;

Chemical Formula 5

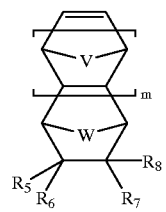

-continued

Chemical Formula 6

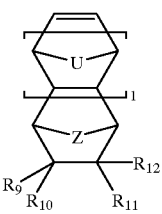

wherein X, Y, V, W, U and Z individually represent oxygen, sulfur, $CH_2$ or $CH_2CH_2$; n represents an integer from 1 to 5, m and 1 individually represent an integer of 0 to 5; $R_1$ to $R_{12}$ individually represent hydrogen, $C_1$–$C_{10}$ alkyl having substituent(s) on its main or branched chain, $C_1$–$C_{10}$ ester having substituent(s) on its main or branched chain, $C_1$–$C_{10}$ ketone having substituent(s) on its main or branched chain, $C_1$–$C_{10}$ carboxylic acid having substituent(s) on its main or branched chain, $C_1$–$C_{10}$ acetal having substituent(s) on its main or branched chain; a, b, c, d and e individually represent polymerization ration of each comonomer which is present; and $R_{13}$ is a linear or branched alkyl group; provided that at least one of $R_1$ to $R_4$ represent(s) —COO—R'—OH wherein R' is an alkyl group with or without substituent(s) on its linear branched chain, at least one of $R_5$ to $R_8$ represent(s) —R"—COO—R wherein R" is a linear or branched alkyl group and R is an acid labile protective group, and at least one of $R_9$ to $R_{12}$ represent(s) —R'"—COOH wherein R'" is a linear or branched alkyl group; and;

(b) adding a metal catalyst to the resultant solution to induce a polymerization reaction.

* * * * *